United States Patent [19]

Gutterson et al.

[11] Patent Number: 5,187,061
[45] Date of Patent: Feb. 16, 1993

[54] TRANSDUCING PARTICLES AND METHODS FOR THEIR PRODUCTION

[75] Inventors: Neal I. Gutterson; William T. Tucker, both of Oakland; Paul K. Wolber, Hayward, all of Calif.

[73] Assignee: DNA Plant Technology Corporation, Oakland, Calif.

[21] Appl. No.: 609,331

[22] Filed: Nov. 5, 1990

Related U.S. Application Data

[63] Continuation-in-part of Ser. No. 474,282, Feb. 5, 1990, which is a continuation-in-part of Ser. No. 253,160, Oct. 4, 1988, abandoned.

[51] Int. Cl.$^5$ ............... C12N 15/00; C12N 7/01; C12N 1/21
[52] U.S. Cl. ................... 435/5; 435/172.3; 435/235.1; 435/252.3; 435/252.33
[58] Field of Search ............... 435/5, 172.3, 235.1, 435/320.1, 252.3; 536/27

[56] References Cited

U.S. PATENT DOCUMENTS

| | | | |
|---|---|---|---|
| 4,464,473 | 8/1984 | Orser et al. | 435/172.3 |
| 4,689,295 | 8/1987 | Taber et al. | 435/6 |
| 4,861,709 | 8/1989 | Ulitzur et al. | 435/6 |

OTHER PUBLICATIONS

Dodson et al. (Mar. 30, 1989), Gene 76, pp. 207–213.
Makela, *Enterobacterial Surface Antigens: Methods for Molecular Characterization*, Korhonen et al., eds. Elsevier Science Publishing, Amsterdam, pp. 155–178 (1985).
Susskind et al. (1978) Microbiol. Rev. 42:385–413.
Watanabe et al. (1972) Virol. 50:874–882.
Orbach and Jackson (1982) J. Bacteriol. 149:985–994.
Schmidt and Schmieger (1984) Mol. Gen. Genet. 196:123–128.
Vogel and Schmieger (1986) Mol. Gen. Genet. 205:563–567.
Spanova and Karlovsky (1986) Folia Microbiol. 31:353–363.
Young et al. (1983) Proc. Natl. Acad. Sci. USA 80:1194–1198.
Viera et al. (1987) Meths. Enz. 153:3–11.
ASM News (1987) 53:542.
Orser et al. *Molecular Genetics of the Bacterial-Plant Interaction* (A. Puhler, ed.), Elsevier/North Holland Biomedical, pp. 353–361 (1983).
Green et al. (1985) Nature 317:645–648.
Corotto et al. (1986) EMBO J. 5:231–236.
Warren et al. (1986) Nuc. Acids. Res. 14:8047–8060.
Wolber et al. (1986) Proc. Natl. Acad. Sci. USA 83:7256–7260.
Vali (1971) J. Atmos. Sci. 28:402–409.

*Primary Examiner*—Richard A. Schwartz
*Assistant Examiner*—Philip W. Carter
*Attorney, Agent, or Firm*—Townsend and Townsend

[57] ABSTRACT

Viable bacteria may be detected in biological samples by exposing bacterial cultures obtained from the samples to transducing particles having a known host range. Such transducing particles carry a heterologous gene capable of altering the phenotype of the bacteria in a readily detectable manner. For example, the transducing particles may carry an ice nucleation gene and the alteration of phenotype may be detected using an ice nucleation assay. By employing a panel of phage, unknown bacteria nmay be typed based on the pattern of reactivity observed. The transducing particles may be prepared by introducing a synthetic transposable element carrying the heterologous gene to a host carrying a prophage having the desired host range. After transposition, the host may be induced to a lytic cycle to release the transducing particles carrying the heterologous gene.

35 Claims, 4 Drawing Sheets

Figure 1. CONSTRUCTION OF TRANSPOSABLE ELEMENT

BT1   5'AATTCTAGAGGCCTGCGGCCGCCTGACTCTTATACACAAGTAGCGAGATCTGATATCCCGGGC 3'

BT2   5'TCGAGCCCGGGATATCAGATCTCGCTACTTGTGTATAAGAGTCAGGCGGCCGCAGGCCTC      3'

```
       XbaI       NotI                              BglII      SmaI
   EcoRI   StuI         Tn5 "outside end"                EcoRV     XhoII
5'AATTCTAGAGGCCTGCGGCCGCCTGACTCTTATACACAAGTAGCGAGATCTGATATCCCGGGC......3'
3'....GATCTCCGGACGCCGGCGGACTGAGAATATGTGTTCATCGCTCTAGACTATAGGGCCCGAGCT..5'
```

Transposon Tn5504

lacZα

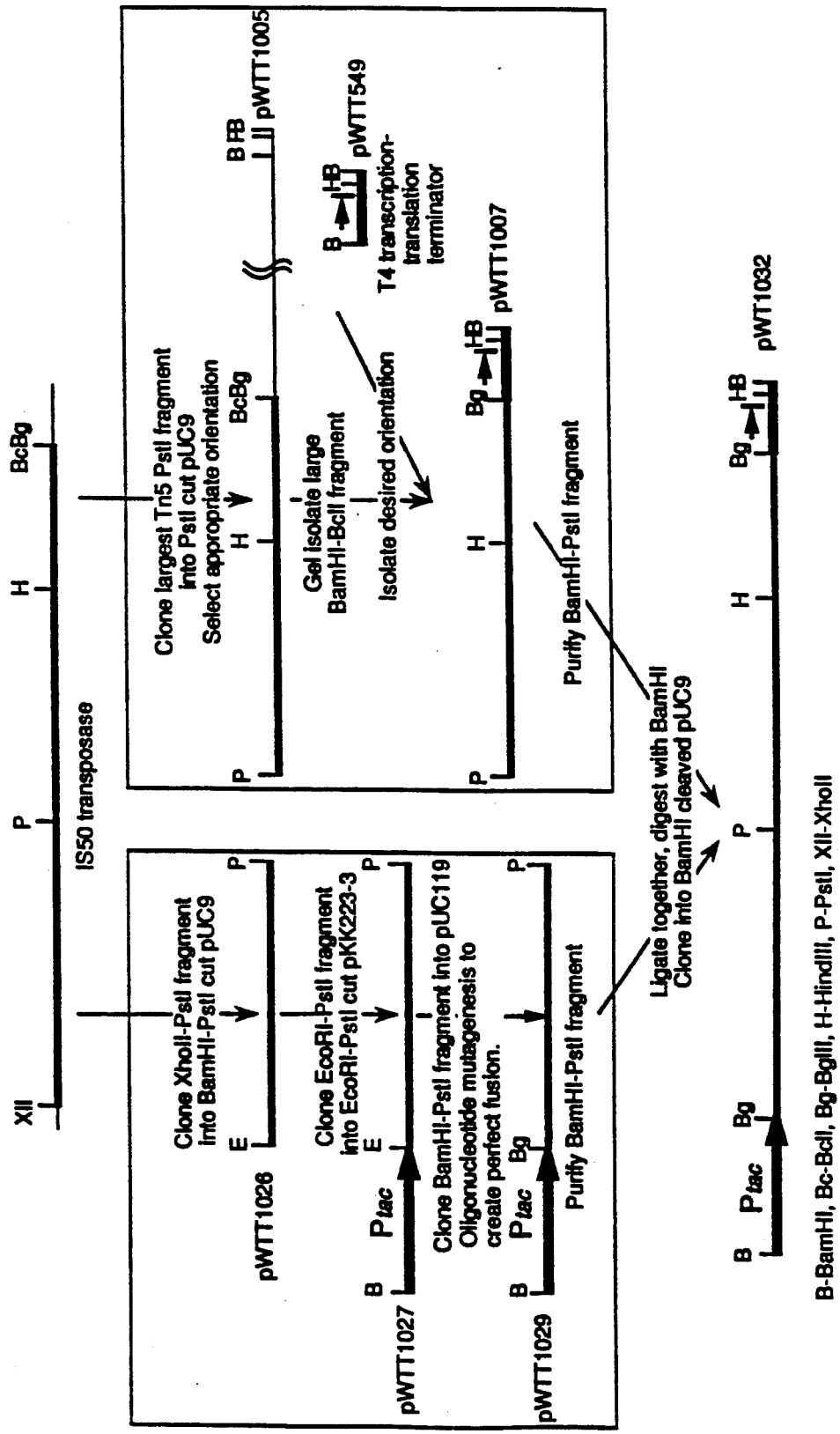
Figure 2. MODIFICATION OF IS50R TRANSPOSASE

Figure 3. CONSTRUCTION OF TRANSPOSON DELIVERY VECTORS
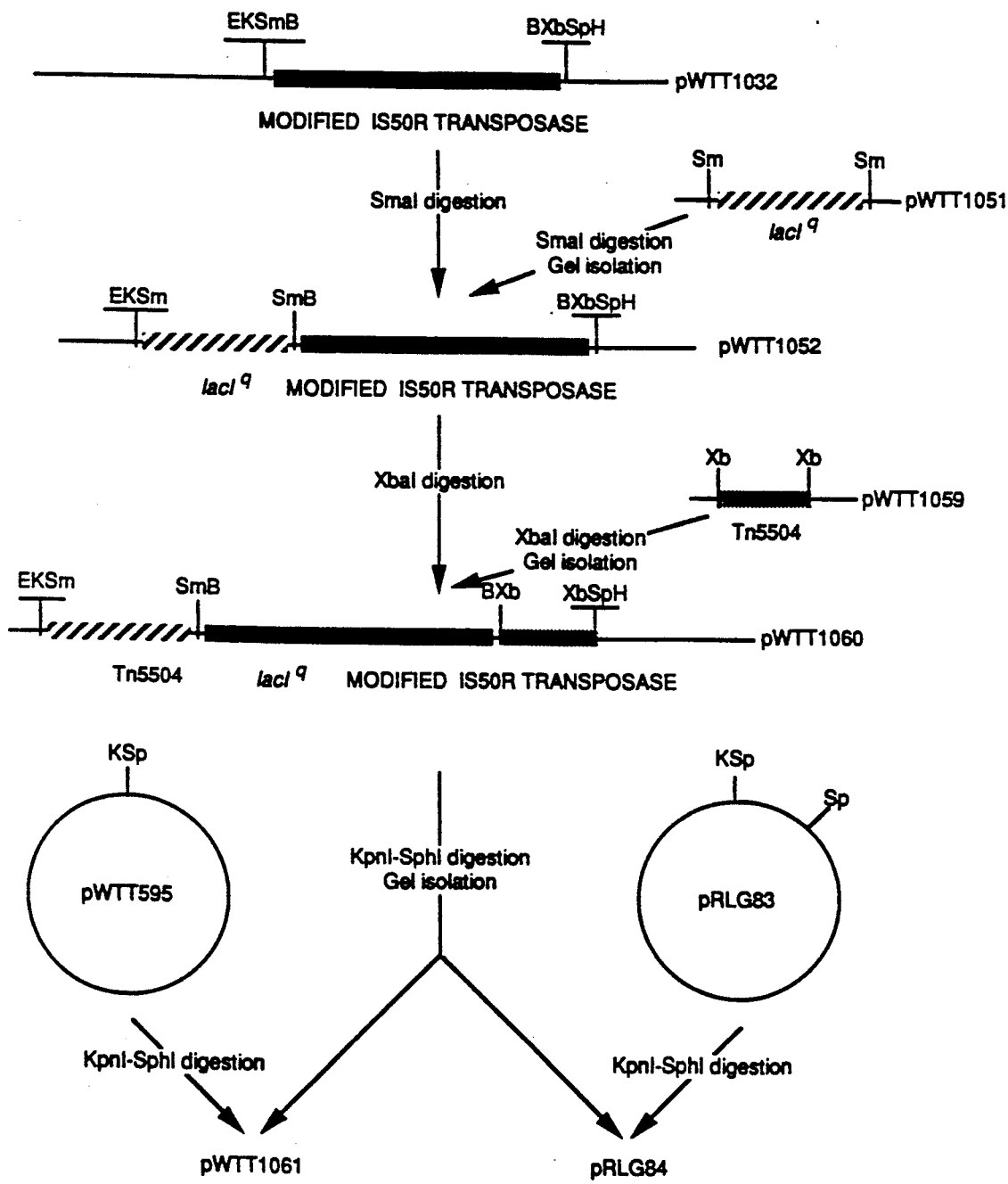

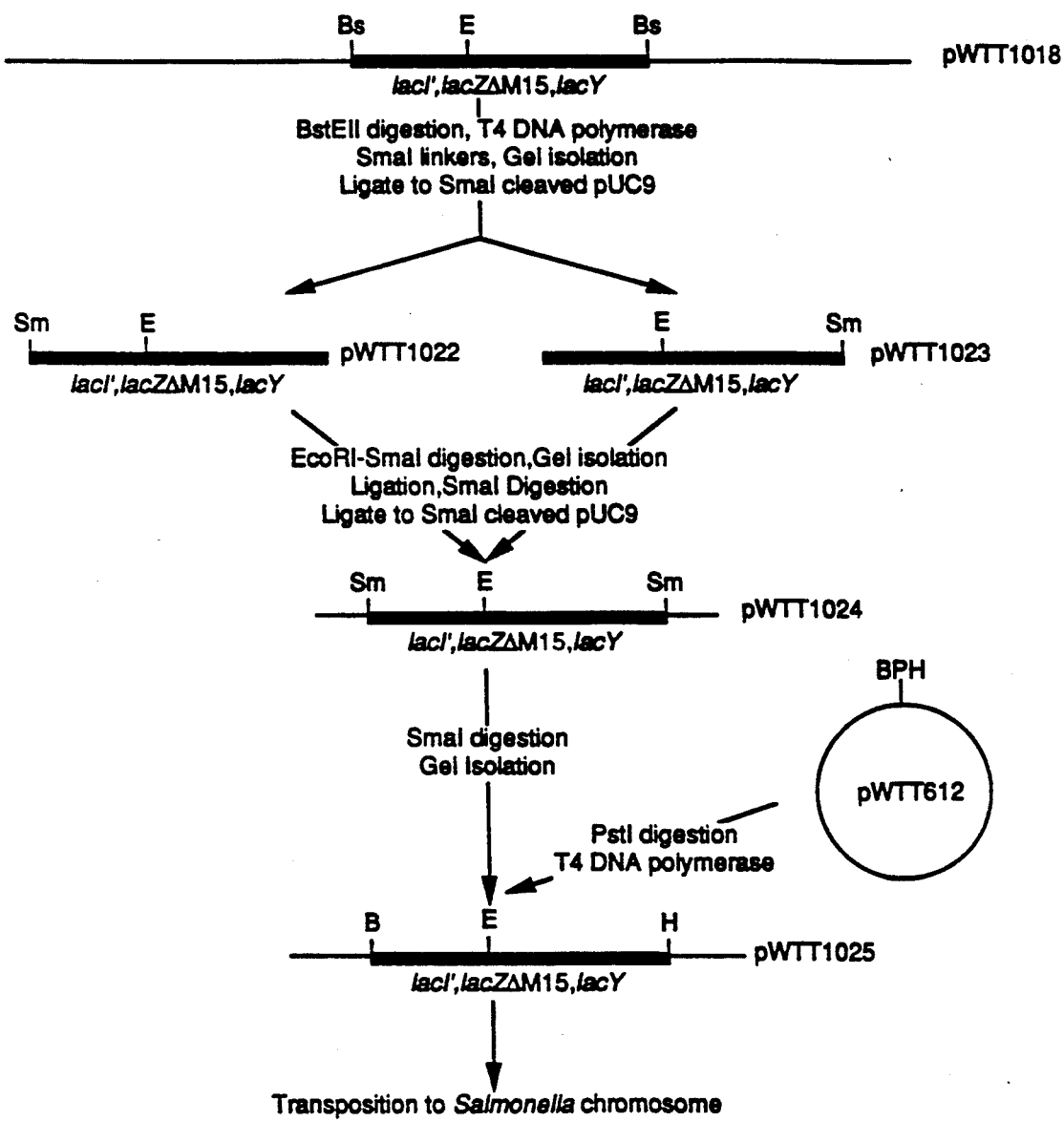
Figure 4. CONSTRUCTION OF lacZΔM15 INDICATOR STRAINS
E-EcoRI, Bs-BstEII, H-HindIII, P-PstI, Sm-SmaI

TRANSDUCING PARTICLES AND METHODS FOR THEIR PRODUCTION

This application is a continuation-in-part of application Ser. No. 07/474,282, filed on Feb. 5, 1990, which was a continuation-in-part of application Ser. No. 07/253,160, filed on Oct. 4, 1988, now abandoned.

BACKGROUND OF THE INVENTION

1. Field of the Invention

The present invention relates generally to the detection and identification of bacteria in biological samples. More particularly, the present invention relates to the preparation and use of a transducing particle capable of specifically infecting cells of interest and transforming the infected cells to a detectable phenotype.

The detection and identification of bacterial species and strains is of interest under a variety of circumstances. For example, there is a need to be able to rapidly screen food, water, and other comestibles for contamination with pathogenic bacteria. The detection of bacteria in patient samples is similarly necessary in the treatment of numerous infectious diseases. In the latter case, it is frequently desirable to be able to specifically type the bacteria and would be further desirable to screen the bacteria for sensitivity to various bacteriocides.

Heretofore, various techniques have been used for bacterial identification, including serotyping, nutritional screening, and phage typing. Serotyping utilizes a panel of antibodies capable of binding to distinct cell surface antigens on target bacteria. Based on the observed pattern of binding, the species and strain of the bacteria may be determined. Nutritional screening relies on variations in the metabolic requirements of different types of bacteria. By growing (or attempting to grow) the bacteria on well-defined media, the bacteria may be classified based on those substances which are necessary for growth and those substances which inhibit growth.

Of particular interest to the present invention, bacteriophage have been used to type bacterial cultures based on the limited host range of different phage. By attempting to infect aliquots of a pure culture of unknown bacteria with a panel of different phage, the bacterial cell type can be determined.

While such phage typing is a highly accurate and determinative procedure for identifying bacterial type, it suffers from being both time consuming and labor intensive. Bacteria in a sample must first be grown out so that pure cultures may be isolated. Individual colonies of the pure cultures must then be grown and subsequently divided into aliquots which are exposed to the different phage in the panel. After exposure, conventional plaque assays are run to determine the infectivity of the various phage. The entire procedure takes from 24 to 48 hours, or longer, and requires highly trained personnel for execution. Because of the lengthy procedure, and the need to identify plaques in the bacterial colonies, the procedure is not amenable to automation. Moreover, because of the time required, the procedure is less than ideal for determining the nature of a patient's infection prior to therapy.

Disabled bacteria, such as those debilitated by cooking or partial heat sterilization, are a major detection problem in many food processing situations. Such disabled bacteria frequently remain viable (and thus potentially pathogenic) yet are sufficiently weakened so that detection by conventional assay protocols may require a non-selective recovery step (pre-enrichment) followed by a selective enrichment step to allow growth of the targeted bacteria while growth of competing organisms is inhibited. Such additional steps can significantly add to the time required to perform the assay.

Detection of particular bacteria in open environments, such as air, water, and soil, can also be problematic. Because of the wide variety of species that may be present, it will often be difficult to distinguish a particular species of interest.

In view of the above, it would be desirable to provide improved phage for detecting and identifying bacterial cells in biological samples. In particular, it would be desirable if such phage were suitable for assays that could be performed in a relatively short period of time and for assay protocols which would be sufficiently simple to be performed by semi-skilled personnel. Preferably, the assays will be performed on mixed cultures, with a minimum number of steps, and result in a detectable event which is easily observed and amenable to automated reading. It would be further desirable if the assays were able to detect partially disabled bacteria which might otherwise require a pre-enrichment step and a selective enrichment step for detection. In addition, it would be desirable to be able to rapidly and conveniently detect particular bacterial cells in open environments, such as air, water, and soil.

2. Description of the Background Art

The use of bacteriophage in characterizing the surface of bacterial cells is discussed in Makela, *Enterobacterial Surface Antigens: Methods for Molecular Characterization*, Korhonen et al., eds., Elsevier Science Publishing, Amsterdam, pp. 155-178 (1985), where conventional plaque assays are employed to determine infectivity of particular phage. The molecular genetics of bacteriophage P22 is discussed in Susskind and Botstein (1978) Microbiol. Rev. 42:385-413. The ability of P22 to act as a transduction vector is described in Watanabe et al. (1972) Virol. 50:874-882 and Orbach and Jackson (1982) J. Bacteriol. 149:985-994. The use of P22 to selectively transduce recombinant plasmids with integrated pac sequences is described in Schmidt and Schmieger (1984) Mol. Gen. Genet. 196:123-128 and Vogel and Schmieger (1986) Mol. Gen. Genet. 205:563-567. Foreign genes are inserted into bacteriophage L (related to P22) by transposon mutagenesis, as described in Spanova and Karlovsky (1986) Folia Microbiol. 31:353-363. The use of λ phage as a cloning vector is described in Young and Davis (1983) Proc. Natl. Acad. Sci. USA 80:1194-1198, where unknown gene products may be detected by antibody probes. The use of M13 phage as a cloning vector is described in Vieira and Messing (1987) Meths. Enz. 153:3-11.

Bacteria may be detected in biological samples by a number of techniques, including selective media, immunoassays, and nucleic acid probes. Particular methods for detecting Salmonella are described in U.S. Pat. No. 4,689,295. A phage-based test for detecting Salmonella in food is described in ASM News (1987) 53:542. The test uses phage to mediate the adsorption of the target Salmonella on a surface.

The ability to nucleate ice formation has been reported to be encoded by a single gene in several ice nucleation-positive (Ina+) bacteria, and this ability can be transferred to *E. coli* by transformation with a plasmid carrying the ice nucleation gene. See, U.S. Pat. No. 4,464,473; Orser et al., *Molecular Genetics of the Bacteri-* al-Plant Interaction (A. Puhler, ed.), Elsevier/North Holland Biomedical, pp. 353–361 (1983); Green et al. (1985) Nature 317:645–648; and Corotto et al. (1986) EMBO J. 5:231–236. Sequence information for an ice nucleation gene in P. syringae (gene inaZ) has been reported; Green et al. (1985) id. The corresponding protein is of approximate molecular weight $1.2 \times 10^5$. Sequence information for an ice nucleation gene in P. fluorescens (gene inaW) has also been reported. See, Warren et al. (1986) Nuc. Acids. Res. 14:8047–8060. Information concerning the identification and purification of the inaZ and inaW proteins is reported in Wolber et al. (1986) Proc. Natl. Acad. Sci. USA 83:7256–7260.

The droplet freezing assay is a known method of testing for the presence of whole cell ice nucleating bacteria and cell-free nuclei. The method consists of laying out an array of N droplets of volume V (usually 0.01 ml) on a nucleus-free surface, cooling to temperature T (less than 0° C.) and scoring $N_f$, the number of droplets frozen. The number of nuclei/ml is then calculated by the following formula: nuclei/ml $= (1/V) \log_e [N/(N-N_f)]$. G. Vali (1971) J. Atmos. Sci. 28:402–409.

SUMMARY OF THE INVENTION

According to the present invention, transducing particles carrying a marker sequence between a pair of transposable element terminal sequences are prepared by introducing DNA sequences to a bacterial host carrying a prophage in its genome. The DNA sequences include both (a) the transposable element terminal sequences having the marker sequence there between and (b) a transposase gene, whereby the marker sequences may become incorporated within the prophage. Usually, the prophage will be present or introduced prior to introduction of the terminal sequences and transposase gene, but it will also be possible to introduce the transposase gene first followed by introduction of the prophage and the terminal sequences. The prophage can then be induced to a lytic cycle whereby the transducing particles carrying the marker sequence are released. By initially maintaining the transposase gene outside of the terminal sequences and inserting the "insertable element", the released transducing particles will lack a transposase gene. The lack of a transposase gene is advantageous since it prevents further transposition events after the insertable element has been transposed to the genome of the bacterial host.

In addition to the transducing particles and methods for producing the transducing particles, the present invention comprises transposable elements and bacterial vectors useful for preparing the transducing particles as well as bacterial hosts carrying transposable elements and marker sequence but free from a transposase gene.

The transducing particles of the present invention are useful for detecting and identifying viable bacteria in biological samples. For these purposes, the term viable bacteria includes all bacteria capable of expressing genes (transiently or otherwise). The compositions comprise bacteriophage particles capable of infecting a known host range of bacteria and transducing such bacteria to a readily detectable phenotype, preferably an ice nucleation phenotype. Transducing particles of the present invention are suitable for detecting most types of bacteria, with the limitation that the target bacteria must be susceptible to bacteriophage infection and the wild-type bacteria cannot itself produce the detectable phenotype. Biological samples of interest may be obtained from virtually any source capable of supporting or preserving bacteria in a viable condition, including patient specimens, water, dairy products, meat products, and the like. Such samples will often contain mixed or impure populations of bacteria, possibly but not necessarily containing a target bacterial species of interest. The transducing particles are particularly useful with samples that have been subjected to sterilization, where the object is to detect viable bacteria which survived such sterilization. The transducing particles of the present invention are capable of detecting partially debilitated (but viable) bacteria which may be present after sterilization, e.g., Salmonella, particularly in food which has undergone sterilization.

The transducing particles of the present invention may be used either for screening samples for the presence of bacteria or for typing bacteria of an unknown strain or species. For screening, one may use a single transducing particle having a relatively broad host range. The biological sample is incubated under conditions suitable for promoting the growth of bacteria, and there is no need to provide a pure culture. Such screening procedures are very rapid and simple and are particularly useful in identifying contaminated samples, such as food or water samples. Bacterial typing, in contrast, utilizes a panel of transducing particles having distinct or overlapping host ranges. Each of the transducing particles tested against a culture (pure or otherwise) of the bacteria, typically by adding various members of the panel to aliquots of the culture to be tested. The type of bacteria is then determined based on the pattern of reactivity of the individual transducing particles. Although typing may involve the use of a pure culture of the bacteria, the method of the present invention has the advantage that the detection of particle infectivity is very rapid, greatly shortening the overall time required for the assay. Moreover, the detectable phenotype, such as ice nucleation, may readily be detected by automated systems, reducing the labor required for the assay.

The transducing particles of the present invention will also find use in following or tracking a modified bacteria which has been released in an environment, typically the ambient environment. The bacteria are first modified to express a cell surface marker recognized by a transducing particle. Bacterial samples from the environment may then be screened with the transducing particle which is capable of conferring a detectable phenotype. The ice nucleation phenotype is particularly preferred because of its sensitivity of detection and low background level in most environments.

The transducing particles of the present invention incorporate the specificity of a natural bacteriophage for particular bacteria. This specificity is retained when the bacteriophage are modified to contain a marker gene to produce transducing particles according to the method of the present invention. As a consequence, detection via an assay utilizing the transducing particles can be accomplished on a specific basis, irrespective of the presence of other (non-target bacteria). Of course, it is possible (although unlikely) that the modified bacteriophage of the present invention may have some change in their host range specificity when compared to the wild type phage from which they have derived. Such variation will not be a problem so long as the bacteriophage retains specificity for the bacteria of interest and is free from specificity for other bacteria which might be present in a particular sample.

An important advantage of the transducing particles of the invention is that they may be used in assays involving bacterial cells which are viable but disabled (physiologically compromised) in some fashion, e.g., by exposure to injurious or debilitating treatments such as heat, cold or desiccation. Such disablement commonly results during industrial processing, e.g., processing of food-borne bacterial contaminants. The transducing particles of the invention are capable of detecting disabled cells, including disabled cells in a mixture of healthy and disabled cells. This provides an important time-saving feature in that it minimizes or eliminates the need for a pre-enrichment step and a selective enrichment step. Such steps are commonly used in other bacterial assays as a means to allow the target cells to multiply to a detectable level while the populations of other organisms are kept in check. See Andrews, *Injured Index and Pathogenic Bacteria*, CRC Press, Boca Raton, Fla., pp. 56-113 (1989). Because debilitated cells may be unable to survive the rigors of selective enrichment, a prior nonselective "pre-enrichment" step is often employed to allow the weakened cells to recover. The FDA Salmonella isolation protocol recommends a minimum of 22 hours for each of the two steps (pre-enrichment and selective enrichment); Andrews et al., *Bacteriological Analytical Manual*, 5th Edition, Food and Drug Administration, District of Columbia, Chapter VI, 1-29 (1978). The composition of the invention thus offers considerable time saving advantages when applied to systems having disabled cells.

In a preferred embodiment, the transducing particle carries an ice nucleation gene. The sample is first incubated with the phage under conditions which promote attachment of the phage to the cell, typically at a temperature in the range from about 35° C. to 40° C. without agitation for a time in the range for about 15 to 120 minutes. Thereafter, the sample is incubated in a suspension under conditions which promote development of the ice nucleation phenotype, typically at a temperature in the range from about 20° C. to 25° C. for a period in the range from about 30 minutes to 2 hours. Bacteria transformed to the ice nucleation phenotype are detected by a conventional cryoassay, typically by dividing the suspension to be tested into droplets having volumes below about 10 μl and exposing the droplets to a temperature in the range from about −3° C. to −12° C., more usually in the range from about −8° C. to −10° C. The formation of ice nuclei in such a temperature range indicates the presence of ice nucleation sites on the cell surfaces of the bacteria.

A particular advantage of the ice nucleation phenotype is that target bacteria may be detected at very low levels, even in the presence of a large excess of viable or non-viable non-target bacteria. Moreover, the sensitivity of the detection method of the ice nucleation assay of the present invention may be increased by decreasing the temperature at which the ice formation is observed. At lower temperatures, fewer ice nucleation positive bacteria are required to cause observable ice nucleation. The formation of ice nuclei resulting from the presence of ice nucleation positive bacteria is a very rapid phenomenon, allowing very rapid assay methods. Finally, the ice nucleation phenotype is extremely rare in nature, allowing assays having very low backgrounds.

BRIEF DESCRIPTION OF THE DRAWINGS

FIG. 1 illustrates the polylinkers used in Example 1 to prepare transposon Tn5504.

FIG. 2 illustrates the preparation of pWT1032 using IS50 transposase as described in Example 2.

FIG. 3 illustrates the construction of transposon delivery vectors as described in Example 4.

FIG. 4 illustrates the construction of a lacZ M15 indicator strain as described in Example 5.

DESCRIPTION OF THE SPECIFIC EMBODIMENTS

The present invention utilizes modified bacteriophage, referred to hereinafter as transducing particles, in order to detect or identify bacterial cells in biological samples. As used herein, the term transducing particles shall also include component parts of a modified bacteriophage which component parts, when mixed together under proper conditions, will combine to form the modified bacteriophage. The biological samples may be virtually any substance or medium capable of supporting bacterial growth or otherwise suspending bacterial cells in a viable state. Biological samples of particular interest to the present invention include water, soil, food samples, such as meat products and dairy products which are particularly susceptible to bacterial contamination, patient samples, such as blood, plasma, serum, sputum, semen, saliva, lavage, feces, cell culture, and the like.

The range of bacterial cells to be detected is limited only by host ranges of available bacteriophage. Of particular interest are pathogenic bacteria which are capable of contaminating food and water supplies and are responsible for causing diseases in animals and man. Such pathogenic bacteria will usually be gram-negative, although the detection and identification of gram-positive bacteria is also a part of the present invention. A representative list of bacterial hosts of particular interest together with the diseases caused by such hosts and the bacteriophage capable of infecting such hosts is presented in Table 1.

TABLE 1

| Bacteria | Gram type | Diseases Caused | Bacteriophage |
|---|---|---|---|
| *Bordetella pertussis* | negative | whooping cough | See, N.A. Pereversev et al. (1981) Zh. Mikrobiol. 5:54-57 |
| *Brucella abortus* | negative | brucellosis | TB; 212; 371 |
| *Mycobacterium tuberculosis* | — | tuberculosis | LG; DSGA |
| *Salmonella typhi* | negative | typhoid fever | 163; 175; ViI; ViVI; 8; 23; 25; 46; 175; F0 |
| *Salmonella typhimurium* | negative | gastroenteritis; septicemia | L; P22; 102; F0 |
| *Salmonella schottmulleri* | negative | gastroenteritis; septicemia | 31; 102; F0; 14 |
| *Salmonella cholerae suis* | negative | gastroenteritis; septicemia | 102 |

TABLE 1-continued

| Bacteria | Gram type | Diseases Caused | Bacteriophage |
|---|---|---|---|
| *Salmonella anatum* | negative | gastroenteritis; septicemia | E15 |
| *Salmonella newington* | negative | gastroenteritis; septicemia | E34 |
| *Salmonella bovismorbificans* | negative | gastroenteritis; septicemia | 98 |
| *Serratia marcescens* | negative | wound infections | S24VA |
| *Shigella dysenteriae* | negative | bacterial dysentery | φ80; P2; 2; 37 |
| *Staphylococcus aureus* | positive | toxic shock, infections | K; P1; P14; UC18; 15; 17; 29; 42D; 47; 52; 53; 79; 80; 81; 83A; 92 |
| *Streptococcus pyogenes* | positive | streptococcal infections | φX240; 1A; 1B; 12/12; 113; 120; 124 |
| *Vibrio cholerae* | negative | cholera | 138; 145; 149; 163 |
| *Yersinia pestis* | negative | plague | R; Y; P1 |
| *Listeria monocytogenes* | positive | meningitis, abcess | 243 |
| *Pseudomonas aeruginosa* | negative | wound and burn infection | B3; pp. 7 |
| *Escherichia coli* | negative | urinary infection | P1; T3; T4; T7 |
| *Klebsiella pneumoniae* | negative | respiratory, urinary infection | 60; 92 |

The transducing particles of the present invention are obtained by modifying a naturally-occurring bacteriophage to carry a gene capable of transforming the target bacteria to an easily recognizable phenotype, referred to hereinafter as the primary marker gene. The transducing particle must be capable of specifically introducing the primary marker gene into the target bacterial host in such a way that the bacterial host can express the gene function in a detectable manner. A large number of bacteriophage exist and may be selected for modification based on the desired host range and the ability of the bacteriophage to carry and transduce the gene of interest. In particular, the bacteriophage must be large enough to accommodate the primary marker gene, associated promoter region, and any other DNA regions which may be included. Modified bacteriophage of the present invention will usually retain the normal host range specificity of the unmodified bacteriophage, although some alteration in specificity would be acceptable so long as it does not affect the ability to identify the selected target bacteria.

The bacteriophage to be modified may be temperate or virulent, preferably being temperate. Modification of the bacteriophage may result in a defective transducing particle which is capable of introducing the marker gene into a target bacterial host, but which is incapable of achieving lytic or lysogenic infection. In this case, the primary marker gene may be part of a plasmid or other self-replicating episomal unit which will be sustained and expressed in the infected host.

Transduction of the marker phenotype may take place via transient expression (i.e., expression from a gene which is not stably inherited by the cell) of the marker gene. In such case, the DNA transduced by the bacteriophage may not survive intact through the entire test period. However, transcription of the marker gene transduced by the phage will be sufficiently efficient before the DNA is degraded to ensure that the bacteria has assembled a functional marker by the end of the test period. The bacteria can thus be detected by the assay of the invention even if the bacteria degrades the phage DNA.

Bacteriophage useful in the present invention may be obtained from microbiological repositories, such as the American Type Culture Collection, 12301 Parklawn Drive, Rockville, Md. 20852. Virulent bacteriophage are available as bacteria-free lysates, while lysogenic bacteriophage are generally available as infected host cells.

Wild-type bacteriophage obtained from any source may be modified by conventional recombinant DNA techniques in order to introduce a desired primary marker gene capable of producing the detectable phenotype of interest. Prior to introduction, the marker gene of interest will be combined with a promoter region on a suitable gene cassette. The gene cassette may be constructed by conventional recombinant DNA techniques in a suitable host, such as *E. coli*. Both the marker gene and the promoter region should be chosen to function in the target host, and the cassette may optionally include a second marker gene, such as antibiotic resistance, heavy metal resistance, or the like, to facilitate in vitro manipulation.

The primary marker gene (or genes, if not a single gene system) should be capable of expressing a screenable phenotype in the target bacterial host. As used hereinafter and in the claims, the phrase screenable phenotype is intended to mean a characteristic or trait which allows cells which express the phenotype to be distinguished from other cells which do not express the phenotype, even when all cells are growing and reproducing normally in a mixed culture. That is, detection of the characteristic or trait may be carried out while the infected target cells are present in mixed population of viable, usually proliferating non-target bacteria which do not express the phenotype. Preferably, the screenable phenotype will comprise a visually observable trait, i.e., one that can be directly or indirectly observed in a mixed population of target and non-target cells. The phenotype will usually not be selectable, i.e., one which provides for survival or preferential growth under particular conditions (positive selection) or which provides for growth inhibition or killing under particular conditions. The method of the present invention does not require that target bacteria present in the sample be isolated from or enriched relative to non-target bacteria which may be present in the sample because the trait will be observable when target bacteria comprise only a portion of the viable bacteria present.

The marker gene can encode the screenable phenotype by itself or may be part of a multiple gene system encoding the phenotype, where other genes are present in or separately introduced to the host to be detected. For example, the phage may carry the lacZα gene which requires a complementary lacZβ gene or lacZΔM15 deletion in the host for expression. See Example 5 hereinafter.

Suitable screenable phenotypes include bioluminescence, fluorescence, enzyme-catalyzed color production (e.g., using the enzyme β glucuronidase (GUS)), ice nucleation activity, and the like. Each of these phenotypes may be observed by conventional visualization techniques which provide the chemical reagents necessary to complete a signal producing reaction. Preferred is the use of ice nucleation activity which is demonstrated herein to be easily and rapidly detectable using conventional ice nucleation assays. While the remainder of this disclosure is directed primarily at the preferred introduction and detection of ice nucleation activity and target bacterial cells, certain aspects of the present invention may be achieved with other detectable phenotypes.

Suitable ice nucleation genes may be isolated from microorganisms which naturally display an ice nucleation phenotype. Exemplary ice nucleation genes and the bacteria from which they may be isolated include inaZ isolated from *Pseudomonas syringae* S203, inaY isolated from *Pseudomonas syringae* PS31, inaW isolated from *P. fluorescens* MS1650, and iceE isolated from *Erwinia herbicola*. The sequence of inaZ is given in Green and Warren (1985) Nature 317:645-648; the sequence of inaW is given in Warren et al. (1986) Nucl. Acid. Res. 14:8047-8060; and the sequence of iceE is given in Warren and Corotto (1989) Gene 25:239-242, the disclosures of which are incorporated herein by reference. See also U.S. Pat. No. 4,464,473, the disclosure of which is incorporated herein by reference. The teachings of these references are sufficient to enable one skilled in the art to isolate an ice nucleating organism from the wild and obtain an ina gene therefrom by conventional cloning and screening techniques.

The transducing particles of the present invention may be prepared by a number of conventional genetic manipulation techniques, including site-directed insertion of the marker gene cassette into the bacteriophage genome, packaging of the plasmid carrying the marker gene or a portion thereof into the bacteriophage coat, transposon mutagenesis, and homologous recombination. The choice among these alternatives depends on the nature of the bacterial host, the nature of the bacteriophage, and the extent to which the bacteriophage has been characterized.

For well characterized bacteriophage, particularly those which have been genetically mapped, it is frequently desirable to place the primary marker gene cassette, including the promoter region and optionally the second marker, into the bacteriophage genome by standard recombinant DNA techniques. After preparing the plasmid in a suitable host as described above, the marker gene cassette is excised and inserted into the desired bacteriophage. Strategies for insertion into λ phage, which may be generalized to other bacteriophage, are described in Young and Davis (1983) Proc. Natl. Acad. Sci. USA 80:1194-1198, the disclosure of which is incorporated herein by reference.

Transducing particles capable of lytic or lysogenic infection are prepared by deletion of non-essential regions of the bacteriophage genome and substitution of the gene cassette. Desirably, the regions deleted and inserted will be approximately the same size so that the packaging may be effected with minimum disruption. In some cases, however, it may be necessary to delete certain essential regions of the bacteriophage genome, particularly when it is desired to insert relatively large marker gene cassettes. In that case, the transducing particles will retain the ability to insert the DNA into the desired bacterial host, but will be unable to reproduce within the host. Reproduction may be obtained, however, by providing a helper bacteriophage, such as the wild-type bacteriophage, which is able to provide essential packaging functions.

Alternatively, for well characterized bacteriophage, it is possible to package the plasmid or the marker gene cassette by attachment of the bacteriophage pac site in a DNA construct with the plasmid or cassette. The pac site may be obtained from the bacteriophage genome and cloned into the plasmid carrying the primary marker gene, promoter region, and optional second marker. The plasmid may then be transferred to a suitable bacterial host which is then infected with a bacteriophage having a defective pac site. The bacterial host will then produce transducing particles having the plasmid and/or marker gene cassette packaged within a bacteriophage coat capable of inserting the plasmid DNA into bacteria of its host range. General methods for cloning pac sites and producing packaging-deficient bacteriophage are described by Vogel and Schmieger (1986) Mol. Gen. Genet. 205:563-567, the disclosure of which is incorporated herein by reference.

For less characterized bacteriophage, transposon mutagenesis may be employed to prepare the transducing particles of the present invention. The method of Spanova and Karlovsky (1986) Folia Microbiol. 31:353-363 for the mutagenesis of phage L (*Salmonella typhimurium*), the disclosure of which is incorporated herein by reference, may be generalized to apply to other transposons, bacteriophage, and bacterial hosts. A marker gene cassette from the plasmid, as described above, is first inserted into a desired transposon by conventional techniques. The modified transposon is then transposed into the desired bacteriophage by simultaneous infection of a suitable host with both the modified transposon and the bacteriophage. The host cells are then incubated until lysis occurs, and the released phage are collected. A fraction of the released phage will be carrying the transposon insert. Host cells free from bacteriophage are then infected with the phage mixture obtained as described above, and cells carrying a detectable marker present on the transposon selected. Unlysed selected cells, in which the bacteriophage carrying the modified transposon has become lysogenic, are then plated on selective media and screened for the desired phenotype. Such selected cells thus contain prophage having the desired primary marker gene under the control of a suitable promoter. Transducing particles may then be obtained by inducing the prophage to a lytic state, which results in cell lysis and release of a large quantity of suitable transducing particles.

The use of a secondary selection marker in the preparation of transducing particles by transposon mutagenesis is helpful, but not required. Phage which have been mutagenized to carry the primary selection marker, for example the ice nucleation gene, may be identified over the background of wild-type phage by performing an appropriate assay, such as a replica plating assay for ice nuclei in the case of the ice nucleation gene. Such screening assays are taught in Lindow et al. (1978) App. Environ. Microbiol. 36:831-838, the disclosure of which is incorporated herein by reference.

In addition to the above techniques, transducing particles may be prepared by homologous recombination resulting in low frequency transducing particles or high frequency transducing particles. Low frequency transducing particles may be constructed from the plasmid carrying the marker gene cassette by first preparing a restriction library of the bacteriophage genome of interest. The restriction fragments from the library are then cloned into the plasmid in a suitable host, resulting in plasmids carrying relatively large regions homologous with the wild-type bacteriophage. Such regions serve as cross-over points in homologous recombination events in a manner well described in the art. The recombinant plasmid is then introduced to a suitable bacterial host, and colonies which express the primary or secondary marker gene are selected for infection with the wild-type bacteriophage. A relatively low percentage of the transducing particles produced by the bacteriophage infection will include the entire plasmid carrying the marker gene cassette as an insert. A fresh bacterial culture is then infected with the mixed transducing particles, and transformed colonies are selected based on the expression of either the primary marker or secondary marker carried by the plasmid.

A specific example of the preparation of low frequency transducing particles capable of specifically infecting S. typhimurium is given in the Experimental section hereinafter as Example 2.

Low frequency transducing particles having a relatively high transduction frequency, usually greater than about 5%, may be used for performing the assay of the present invention. For transducing particles having a lower rate of transduction, it will usually be desirable to further modify the bacterial hosts to produce high frequency transducing particles.

High frequency transducing particles are prepared as described above, but employing a prophage in the bacterial genome as the target for homologous recombination. To this end, a lysogenic strain (a strain carrying the wild-type bacteriophage DNA in its genome as a prophage) is employed and transformed with a plasmid carrying the gene marker cassette which is incapable of replication in the host. Thus, only hosts where the selective markers have been incorporated in the prophage will be viable under the appropriate selective conditions. Alternatively, the plasmid may be otherwise altered so that recombination with the prophage is readily detected. Plasmids incapable of replicating in the desired bacterial host may be prepared by several techniques. For example, low frequency transducing phage prepared as described above may be utilized as the immunity functions expressed by the prophage will prevent replication. Second, plasmids capable of replication in a suitable cloning host but incapable of replication in the target host of interest may be used. Finally, the plasmid may be modified so that the primary marker gene is inserted into the prophage, while the secondary marker is placed outside the region which is incorporated in the prophage. Recombination may then be detected by screening for cells which express the primary selection phenotype, but which have lost the secondary selection phenotype. Incorporation of the desired marker gene into the prophage may be confirmed by standard techniques, such as Southern blotting as described in Southern (1975) J. Molec Biol. 98:503-517.

A specific example of a high frequency transducing particle capable of specifically infecting S. typhimurium is given in the Experimental section hereinafter as Example 3.

A preferred means of making a high frequency transducing particle via homologous recombination involves the use of transposon tagging where an insertable element comprises the gene for a detectable phenotype of interest joined to the essential terminal sequences of a transposon. Such insertable elements will be able to identify sites in a bacteriophage genome into which an ice nucleation or other reporter gene can be inserted without interfering with essential bacteriophage functions. In general, any bacterial transposon can be used to prepare the insertable element. It is desirable that the size of the resulting insertable element be as small as possible to allow packaging of the entire resulting phage genome into mature viral particles.

As the frequency of occurrence of suitable sites in transposon tagging is expected to be low, the bacterial transposon used preferably encodes functions that allow for the selection of transposition events. To this end, a naturally occurring transposon may be modified to provide a small-sized, selectable transposon. Any transposon in which the transposase functions can be separated from the ends of the transposable element would be suitable. These include but are not limited to IS (insertion sequence) elements, such as IS50, and transposable drug resistance elements, such as Tn3, Tn5, and Tn7, as is known in the art. The bacterial transposon Tn5 is most convenient for such modifications as it has been characterized in great detail in the art. Krebs and Reznikoff, (1986) J. Mol. Biol. 192:721-791; Dodson and Berg, (1989) Gene 76:207-213.

As one approach, the essential terminal DNA sequences of a transposon can be synthesized chemically by methods known in the art. In synthesizing these DNA sequences, it is advantageous to include flanking sequences (polylinkers) that contain the recognition sites for a number of restriction endonucleases. This facilitates the insertion of selectable markers between the ends of the transposon element, and allows the element thus created to be easily cloned into a vector plasmid, the choice of which depends on the nature of bacterial host for the particular bacteriophage. As is well known in the art, narrow host range plasmids derived from ColE1, P15A, or pMB9 replicons (such as pAT273, pACYC184, pBR322, or pUC19) would be suitable for use in bacteria from the family Enterbacteriaceae, while in general, any broad host range plasmid derived from the incompatibility groups IncP, IncW or IncQ (such as those derived from pRK2, pS-a or pRSF1010) would be suitable for use in other gram negative bacteria. For gram positive bacteria other suitable plasmid vectors known in the art can be used.

It is preferred that the transposase for the chosen transposon not be located between the ends of the transposon. In this way, once the transposable element has been inserted in the bacteriophage genome, it will be unable to undergo a second transposition event. In general, it is also desirable that this location be on the same DNA molecule as the element to be transposed (i.e., in cis), although the transposon and the transposase could, in some systems, be located on separate plasmid replicons (i.e., in trans).

It may also be desirable to modify the expression of the transposase gene of the transposable element by inserting the coding sequence for the transposase protein downstream of a highly expressing bacterial promoter. Such promoters are known to those of skill in the art, and include the tac, trc and lac promoters of E. coli. It is known that overexpression of bacterial transposases can be deleterious to the host cell, so it is also desirable that the transcription from the chosen promoter be capable of regulation. Promoters such as the tac, trc and lac promoters are repressed by the lac repressor, the product of the lacI gene. Inclusion of such a gene on the same molecule as the transposase will ensure expression of the transposase protein only under conditions in which repression is eliminated (i.e., inducing conditions). For the lacI gene, the chemical isopropylthiogalactoside (IPTG) tends to be lac repressor limiting.

In general, any combination of a highly expressing yet repressible promoter and its associated repressor gene will function to give the same result. If a selectable marker is used as an insert between the ends of the transposable element, the marker should be as small as possible. It is preferred that the size of the transposable element be less than 1 kilobase. In general, antibiotic resistance genes are larger than is desirable, although the absolute size of the transposed DNA is determined by the packaging limits of the individual bacteriophage.

A preferred means of selection uses the phenomenon of α-complementation to lactose utilization as described in E. coli. Here, a small fragment of the β-galactosidase gene (the lacZ α fragment which is approximately 500 base pairs in length) encodes a polypeptide which restores functionality to another mutant polypeptide in which amino acids have been deleted (the M15 deletion). The inclusion of the lacZ α fragment between the ends of the transposon allows for the selection of bacteriophage carrying the inserted DNA by their ability to restore lactose utilization to host bacteria which carry the lacZM15 deletion either in the chromosome or on a plasmid that exists in unit copy number per chromosome (e.g., the F factor). The DNA fragments encoding these two activities have been characterized in detail and can be readily manipulated by those skilled in the art. See, I. Zabin et al., The Operon (eds. J. H. Miller et al.), Cold Spring Harbor Laboratory (New York), 104–107 (1978).

A plasmid containing the transposase, end piece DNA, marker DNA and repressor, as described above, is introduced into a bacterial cell (e.g., Salmonella) containing within the bacterial genome prophage DNA (e.g., P22). The transposase is induced by an appropriate chemical inducer (e.g., IPTG) and the bacterial cells are grown for a number of generations. The prophage is then induced, e.g., with an appropriate chemical inducer (e.g., mitomycin C) yielding bacteriophage. The bacteriophage which carry a transposon insertion are selected by infecting a suitable bacterial host (e.g., carrying M15 deletion) with the induced phage lysate. Infected cells are plated out on media selective for the marker (e.g., lacZ α), resulting in selection of cells containing a prophage genome which in turn contains the transposon fragment containing end pieces and marker. The selected cells are then induced for phage lysis to obtain pure phage preparations. The ice nucleation gene is then introduced into the prophage genome by homologous recombination. A plasmid is constructed which carries a copy of the transposable element but which lacks the transposase gene. Preferably, the replication of this plasmid is conditional, such that homologous recombination between the transposon sequences present on the plasmid and in the prophage can be detected by selecting for the antibiotic resistant phenotype of the plasmid under conditions that prevent the plasmid from replicating. Suitable conditional replicons are known to those skilled in the art and include plasmids derived from the group comprising plasmids pSC101, RP4, and F. The ice nucleation gene is inserted in vitro into the sequences of the transposable element present on the plasmid at a convenient restriction enzyme cleavage site to create a "marker exchange" plasmid. The plasmid so created is then introduced into a bacterial strain carrying a prophage bearing a copy of the transposon. Homologous recombination can then be carried out using the plasmid containing the ice nucleation gene so prepared where the homologous recombination involves recombination between transposon sequences present in the prophage DNA in the bacterial genome and the transposon sequences flanking the ice nucleation gene present on the plasmid. The resultant strain, upon phage induction, yields transducing particles containing ice gene DNA at a site within the prophage DNA where the presence of the ice gene at that site does not disrupt essential phage functions.

Transducing particles prepared as described above are used to detect target bacteria in biological samples as follows. In some instances it will be possible to infect a biological sample and observe the alteration and phenotype directly, although in other cases it may be preferred to first prepare a mass culture of the bacteria present in the sample. Methods for obtaining samples and (if necessary) preparing mass culture will vary depending on the nature of the biological sample, and suitable techniques for preparing various sample types are described in detail in standard microbiology and bacteriology texts such as Bergey's Manual of Determinative Bacteriology (8th ed.), Buchanan and Gibbons (eds.) Williams & Wilkens Co., Baltimore (1974); Manual of Methods for General Bacteriology, Gerhardt et al. (eds.), Am. Soc. Microbiology, Washington (1981); and Manual of Clinical Microbiology (2nd ed.), Lennette et al. (eds.), Am. Soc. Microbiology, Washington (1974).

Once the biological sample has been prepared (with or without growth of a mass culture), it will typically be exposed to transducing particles under conditions which promote binding of the particles to the bacteria and injection of the genetic material, typically at a temperature which supports rapid growth of the bacteria (e.g., 35° C. to 40° C.) without agitation for a time sufficient to allow infection (e.g., 15 minutes to 120 minutes). For transducing particles carrying an ice nucleation gene, the sample is then incubated at a lower temperature (e.g., 20° C. to 25° C.) to permit formation of ice nucleation sites. After a short time, typically 30 minutes to 2 hours, the sample may be assayed for ice nuclei as described in more detail below.

For transducing particles carrying an ice nucleation gene, conventional droplet freezing assays as described in Vali (1971), supra., may be useful to detect transformation to the ice nucleation phenotype. Alternatively, a specific fluorescence freezing assay for detecting the ice nucleation phenotype is taught in U.S. Pat. No. 4,784,943, the disclosure of which is incorporated herein by reference. Briefly, the assay for detecting ice nucleation comprises use of fluorescent compounds which in aqueous state manifest a change in fluorescence or visible properties upon freezing or thawing of the aqueous medium. Suitable fluorescent compounds may be selected from the fluorescein family, e.g., calcein, carboxyfluorescein, and related compounds.

The method of the present invention will be used most frequently to screen for a specific type of bacteria (as determined by the host range of the transducing particle) in a mixed population of bacteria derived from a biological sample as described above. The mixed bacterial populations need not be selected prior to screening. Preparation of the sample prior to screening will generally not provide a homogeneous bacterial population, although it is possible to combine the screen of the present application with nutritional selection as described below.

In contrast to conventional phage transduction techniques intended to produce homogeneous colonies of transduced bacterial cells, the method of the present invention does not require that the transduced bacteria be isolated in any way. Instead, the screenable phenotype, e.g., a visually observable trait, conferred by the primary marker gene can be detected in a non-selected portion of the biological sample where viable, usually proliferating, non-target bacteria will be present. The screening can occur without selection since there is no need to isolate the transduced bacteria.

As described above, the assay of the present invention is useful for screening biological samples to determine whether bacteria present in the host range of the transducing particle are present. The present invention is also useful for typing bacterial species and strains in a manner similar to conventional phage typing which instead relies on much slower plaque assays for determining phage infection.

For typing according to the present invention, a panel of transforming particles having differing, usually overlapping, host ranges are employed. The species and strain of the target bacteria (usually present in a substantially pure culture) may then be determined based on the pattern of reactivity with the various transforming particles. Often, such tests may be run on a single carrier, where the different transforming particles are spotted in a fixed geometry or matrix on the carrier surface. The pattern of reactivity may then be rapidly observed. In contrast to the previously-described screening methods, these typing methods will be useful in characterizing homogeneous bacterial cultures (i.e., contained on a single species or strain) as well as typing target bacteria in mixed populations.

The present invention may be combined with nutritional screening in order to further characterize the bacteria being investigated. By providing a selective medium during either the mass culture or the plating culture, the range of bacteria which can remain viable may be limited. As the phenotypic assay of the present invention can only detect viable cells, absence of a detectable phenotype limits the type of bacteria which may be present. By properly combining the host range of the transducing particles and the viability range of the selective medium, the method of the present invention can be made very specific for the type of bacteria being determined.

A second approach for increasing the ability of the present invention to specifically identify bacterial hosts involves the use of immunoadsorption. Immobilized antibodies, including antisera or monoclonal antibodies, are utilized to specifically capture bacterial cells based on the identity of their cell surface epitopes. The bacteria may then be further detected using the transducing particles of the present invention, as described above. Suitable materials and methods for the immunoadsorption of particular bacterial species and strains on solid phase surfaces are described in Enterobacterial Surface Antigens: Methods for Molecular Characterization, Korhonen et al. (eds.), Elsevier Science Publishers, Amsterdam (1985).

The present invention can be particularly useful in patient diagnosis as it allows the determination of bacterial sensitivity to antibiotics and other bactericides. By performing a short incubation of the bacteria with an antibiotic or bactericide to be screened prior to exposure to the transducing particles of the present invention, the metabolic activities of the cells will be halted and the alteration of phenotype prevented. Such testing will be useful after the presence of the bacteria is initially confirmed using the transforming particles as described above. Antibiotics and bactericides which are determined to be lethal to the bacterial infection may then be employed for treatment of the patient. Such rapid and early detection of useful antibiotics and bactericides can be invaluable in treating severe bacterial infections.

Similarly, the present invention can be useful in detecting the presence of antibiotics, e.g., antibiotic residues in animal products. In this approach, an extract of the material to be analyzed is added to a culture of a bacterial strain sensitive to the antibiotic in question, and the mixture is incubated for a period predetermined to be sufficient to kill the strain if a given amount of antibiotic is present. At this point, transducing particles of the invention specific to the strain are added, and the assay of the invention is performed. If the given amount of antibiotic is present, the cells of the bacterial strain will be dead and the read-out will be negative (i.e., lack of freezing in a freezing assay). If the given amount of antibiotic is not present, cells of the bacterial strain will survive and the read-out will be positive (i.e., freezing in a freezing assay).

In a specific embodiment, a means is provided for assaying bacteria which have been previously rendered susceptible to bacteriophage of the invention on a phage-specific basis. That is, in a first step, the target bacteria are modified, e.g., by transformation, so that they contain or express a cell-specific receptor for the bacteriophage of interest. In a second step, the modified (or tagged) bacteria are introduced into, or mixed into, a sample environment in which they are to be followed. The sample environment can be any setting where bacteria exist, including outdoors (e.g., soil, air or water); on living hosts (e.g., plants, animals, insects); on equipment (e.g., manufacturing, processing or packaging equipment); and in clinical samples. The bacteriophage assay of the invention (as described previously) can then be carried out, using bacteriophage specific for the introduced receptor, and the presence of the tagged bacteria can be monitored or quantified.

An advantage of this embodiment is that it provides a means to follow or track bacteria to be released into a sample environment which already contains the same type of bacteria (or closely similar bacteria) or which may be subject to introduction of the same type of bacteria (or closely similar bacteria) from a separate source. The bacteria being tracked can be distinguished from the other bacteria (i.e., bacteria which are essentially the same) by virtue of the presence of the cell-specific receptor which has been introduced into the bacteria being tracked. There is thus provided the opportunity of assaying for the presence of released bacteria in the presence of otherwise identical (but for the receptor component) bacteria, without cross reactivity (background).

An exemplary approach for monitoring Pseudomonas uses the lamB gene of *E. coli* which is known to be a receptor for the coliphage λ. See, G. Vries et al. (1984) Proc. Natl. Acad. Sci. USA 81:6080–6084, and R. Ludwig, (1987) ibid. 84:3334–3338, both of which are incorporated herein by reference. Expression of lamB renders Pseudomonas species susceptible to attachment of λ phage and injection of phage DNA. A recombinant λ phage carrying a reporter gene, e.g., an ice nucleation gene, usually under the control of a strong promoter, is constructed in a broad host range plasmid. A lamB gene is inserted (e.g., by homologous recombination) into the chromosome of the bacteria to be assayed. The assay is then conducted in accordance with the teachings herein.

One specific use of this approach is to monitor Pseudomonas bacteria (e.g., *P. syringae*), including Pseudomonas soil bacteria and Pseudomonas epiphytic bacteria, which are released into a specific environment or setting, e.g., soil, a greenhouse or field setting. At least some of the bacteria to be released are first transformed to express the bacteriophage-specific receptor. Then by collecting bacteria from the environment at a later time, the presence of the bacteria in the environment can be determined. The approach provides a means to follow the presence, the migration and the survivability of the bacteria.

The following examples are offered by way of illustration and not by way of limitation.

EXPERIMENTAL

Standard Media and Methodology

In the plasmid constructions detailed below, the following standard media were used. Bacteria were grown on LB agar (Miller, 1972, Exp. in Mol. Genetics, CHS Publications, Cold Spring Harbor, N.Y.)) and supplemented with antibiotics as indicated. The antibiotics were included at the following final concentrations: Ampicillin, 75 μg/ml; Chloramphenicol, 50 μg/ml; Gentamycin, 20 μg/ml; Kanamycin, 50 μg/ml; Spectinomycin, 100 μg/ml; Streptomycin, 100 μg/ml; chromogenic substrate 5-bromo-4-chloro-3-indolyl-beta-D-galactoside (Xgal), and the non-metabolizable inducer isopropylthiogalactoside (IPTG; Miller, 1972, supra) were used to detect the presence of the lacZα gene fragment.

Unless explicitly stated, standard methods (Maniatis et al., 1982, Cold Spring Harbor Publications, Cold Spring Harbor, N.Y.) were used in all DNA manipulations. Restriction digests were routinely performed in TA buffer (Wartell and Reznikoff, 1980, Gene 9:307–319) or the buffer recommended by the enzyme supplier, unless otherwise stated. Ligation reactions were performed in 1×TA buffer supplemented with ATP at a final concentration of 10 mM. The screening of putative recombinant plasmids was routinely performed on small-scale preparations of plasmid DNA prepared by a modification of the method of Birnboim and Doly (Nuc. Acid Res., 7:1513–1523, 1979), as described by Maniatis et al. (1982), supra.

EXAMPLE I. CONSTRUCTION OF THE TRANSPOSABLE ELEMENT

The essential 19 base pair (bp) terminal sequences of the transposable element Tn5 (Phadnis and Berg, Proc. Nat. Acad. Sci. USA 84:9118–9122, 1988; Makris et al., Proc. Nat. Acad. Sci. USA 85:2224–2228, 1988) were synthesized chemically as two 60-mer oligonucleotides using phosphoramidite chemistries on an Applied Biosystems Model 318A DNA Synthesizer. The sequence of the oligonucleotides is shown in FIG. 1. The sequences include sites for the action of the indicated restriction endonucleases (polylinker sequences) which facilitate the manipulation of these terminal elements.

To create a double-stranded DNA linker fragment from the two oligonucleotides shown in FIG. 1, 100 pmol of each oligonucleotide was mixed in a final volume of 50 μl TE buffer, heated to 60° C. and allowed to cool slowly to room temperature. The mixture was then phosphorylated by addition of 5 μl of linker-kinase buffer (Maniatis et al., supra), 5 μl, $\nu^{32}P$ ATP and 5 U T4 polynucleotide kinase followed by incubation at 37° C. for 1 h.

The initial transposable element was created by using the linker described above to insert a DNA fragment from the plasmid pWTT577 (U.S. patent application Ser. No. 07/357,492, the disclosure of which is incorporated herein by reference) carrying the lacZα fragment from pUC9 (Vieira and Messing, Gene 19:259–268, 1982) and the nptII gene from Tn5 (Jorgensen et al., Mol. Gen. Genet. 177:65–72, 1979).

To create this element, 10 μg of plasmid pBR322 (Bolivar et al., Gene 2:95–113, 1982) was first digested With EcoRI in 50 μl TA buffer. To this was added 25 μl of the kinased oligonucleotide linker, 15 μl H2O, 5 μl 10×TA buffer and 5 μl T4 DNA ligase (120U/μl). The mixture was incubated for 4 h at room temperature, extracted with an equal volume of a phenol:chloroform (P:C, 1:1) mixture, and the aqueous phase precipitated by the addition of 2 volumes of ethanol. The precipitated DNA was dissolved in 100 μl TA buffer and digested with 100 U XhoI for 2 h at 30° C.

The 2 kilobase (kb) lacZα-nptII (lacKm) fragment from pWTT577 was purified from 10 μg of XhoI-digested plasmid DNA by excising the DNA band from a low melting temperature (LMT) agarose gel, extracting the DNA with an equal volume of buffer saturated phenol and ethanol precipitation. The DNA pellet was subsequently dissolved in 25 μl TE buffer.

The two DNA preparations described above were ligated as follows: 5 μl pBR322-linker DNA, 15 μl pWTT577 XhoI lacKm fragment, 2.5 μl 10×TA buffer, 2.5 μl 10 mM ATP and 1 μl T4 DNA ligase (120U/μl) were incubated overnight at room temperature. A 10 μl aliquot of the mixture was transformed into competent cells of *E. coli* strain JM109 (Yanisch-Perron et al., Gene 33:103–119, 1985) prepared as described in Maniatis et al. (supra) and blue kanamycin-resistant colonies selected on L-agar plates containing the chromogenic indicator Xgal and the inducer IPTG.

Plasmid DNA from twelve such colonies was screened by restriction endonuclease digestion with EcoRI and XhoI. Of the clones screened, 10 harbored plasmids which gave an XhoI fragment of the same size as pWTT577 and also gave an EcoRI fragment of a size consistent with the introduction of the lacKm fragment between two linker DNA elements. One colony was saved and the plasmid therein designated pWTT1003.

The transposable element so created was given the designation Tn5500.

The transposable element to be used in the identification of suitable sites for introduction of the inaW gene into bacteriophage genomes was created from Tn 5500 by the substitution of a 452 base pair HaeII DNA fragment carrying the lacZα gene from pUC9 in place of the lacKm fragment present in Tn5500. This was achieved by first replacing the lacKm element with a DNA fragment encoding resistance to gentamycin.

This fragment was isolated from the plasmid pPH1JI (Hirsch and Beringer, Plasmid 12:139–141, 1984) as a HindIII-SphI fragment, cloned into the plasmid pUC19 to create the plasmid pLVC42 subsequently manipulated by the addition of SmaI linkers to T4 DNA polymerase-treated HindIII-SphI-cleaved DNA to create a fragment which can be excided with the enzyme SmaI. This fragment was inserted into the plasmid pUC9 to create the plasmid pWTT623.

For this series of manipulations, the transposable element Tn5500 was inserted as an EcoRI fragment into the EcoRI site of the plasmid pLVC18 (Warren et al. in Advances in the molecular genetics of the bacteria-plant intraction. eds Szalay and Legocki, Cornell University Publishers, Ithaca, N.Y., pp212–214, 1984). The fragment was isolated from a LMT agarose gel as described earlier and ligated to EcoRI-cleaved pLVC18 DNA overnight at room temperature. The ligation mix was transformed into competent cells of *E. coli* strain JM109 and blue, kanamycin, Xgal and IPTG. Four colonies were examined for plasmids carrying the appropriate sized DNA fragments and one such colony having the expected DNA structure was saved and designated pWTT1011.

The SmaI fragment encoding gentamycin resistance was substituted for the lacKm fragment of Tn5500 by digestion of pWTT1001DNA with SmaI and ligation to gel purified DNA of the SmaI gentamycin resistance fragment from pWTT623. Approximately 1 µg of each DNA preparation was ligated together overnight as before and transformed to competent cells of *E. coli* strain HB101 (Boyer and Rolland-Dussoix, J. Mol. Biol., 41:459, 1969). Gentamycin-resistant cells were selected on LB agar plates containing 20 µg/ml gentamycin. The gentamycin-resistant colonies were screened for their tetracycline resistance phenotype, and plasmid DNA from a doubly resistant colony was analyzed by SmaI restriction enzyme digestion. The plasmid DNA had the structure expected for the insertion of the SmaI fragment. This plasmid was designated pWTT1021, and the transposable element so created, Tn5502.

An XbaI fragment carrying Tn5502 was inserted into the XbaI site of the vector pUC119 (Vieira and Messing in Methods in Enzymology eds Wu and Grossman 153:3–11, 1987) to create plasmid pWTT635. To achieve this, the approximately 2 kb XbaI fragment from 5 µg pWTT1021 was purified from a LMT agarose gel as before, and ligated to 1 µg XbaI-cleaved pUC219 DNA. The mixture was transformed into HB101 cells and ampicillin-resistant, gentamycin-resistant colonies screened for the presence of the correct plasmid construction by XbaI restriction enzyme digestion. One plasmid having the desired structure was designated pWTT635.

The lacZα encoding fragment from pUC9 was isolated from 5 µg DNA by digestion with HaeII and subsequent treatment with T4 DNA polymerase to create flush ends. The fragment was purified by elution from a 8% polyacrylamide gel. The DNA was ligated to 1 µg EcoRV-cleaved pWTT635 plasmid DNA, and transformed into cells of JM109. Twelve blue, ampicillin-resistant colonies were selected and screened for plasmid structure by digestion with BglII, and a plasmid with the correct fragment pattern was designated pWTT1059, and the transposable element so created Tn5504.

EXAMPLE 2. CONSTRUCTION OF REGULATED TRANSPOSASE GENE

The regulatory and coding sequences of the IS50R transposase have been identified by others (Krebs and Reznikoff, J. Mol. Biol., 192:781–791, 1986). To facilitate the transposition of the element Tn5504, the transposase of the insertion sequence IS50R was engineered to be highly expressed from the synthetic tac promoter (de Boer et al., Proc. Nat. Acad. Sci. USA, 80:21–25, 1983). This promoter is repressed by the lacI gene product which is itself inactivated by the presence of lactose or synthetic inducers such as IPTG. Thus, the expression of the transposase can be regulated in the presence of the lacI gene product by the addition of IPTG or lactose. Also, a transcription-translation terminator sequence from phage T4 (Prentki et al. supra) was added to the 3' end of the transposase gene to prevent read-through transcription of adjacent sequences from the tac promoter.

Manipulations of the 5' and 3' portions of the transposase gene were performed independently, and the complete gene reconstructed from the two engineered fragments by ligation (see FIG. 2).

The 5' end of the IS50R transposase was isolated as an XhoII-PstI restriction enzyme-cleaved fragment from a complete Tn5 element carried on plasmid pWTT1000. 5 µg of plasmid DNA was digested with XhoII and PstI and the fragment with the size predicted from the nucleotide sequence excised from an 8% polyacrylamide gel. The DNA was eluted from the gel by incubating overnight at 37° C. in a buffer composed of 0.5M ammonium acetate, 1 mM EDTA. The DNA was P:C extracted, ethanol precipitated, and the pellet dissolved in 25 µl TE buffer. 10 µl of this preparation was ligated to approx. 1 µg of pUC119 DNA had previously been digested with BamHI and PstI and also treated with alkaline phosphatase. The ligation mix was transformed into competent cells of *E. coli* strain JM109 and white, ampicillin-resistant colonies selected on LB agar plates containing 75 µg/ml ampicillin, Xgal and IPTG. Plasmid DNA from 6 such colonies was screened by digestion with the restriction enzymes EcoRI and PstI for a fragment of the appropriate size. All six plasmids contained the correct fragment. One was saved as pWTT1026.

To juxtapose the tac promoter to the 5' end of the transposase, the EcoRI-PstI fragment from pWTT1026 was ligated to EcoRI-PstI-cleaved DNA of plasmid pKK223-3 (Brosius and Holy, Proc. Nat. Acad. Sci. USA, 81;6929–6933, 1984). The 5' transposase fragment was purified by excision from a LMT agarose gel as described previously. This DNA was ligated overnight to 1 µg of pKK223-3 DNA which had been cut with EcoRI and PstI and treated with alkaline phosphatase. The mixture was transformed into JM109, ampicillin-resistant cells selected and plasmid DNA from 6 such colonies screened for the presence of an EcoRI-PstI fragment of the desired size, and the presence of a Bam- HI-PstI fragment of a size consistent with the addition of the tac-promoter fragment to the 5' end of the transposase. All six had the desired structure, and one was saved as pWTT1027.

To optimize the synthesis of the transposase, a site-directed deletion was made to place the transcription initiation signals of the tac promoter the optimum number of nucleotides from the translational start of the transposase coding sequence. To accomplish this the BamHI-PstI fragment from pWTT1027 was recloned into the vector plasmid pUC119. This plasmid can be used to create single stranded DNA suitable for oligonucleotide-directed mutagenesis. The appropriate BamHI-PstI fragment from pWTT1027 was purified from LMT agarose as described before, and ligated to BamHI-PstI-cleaved pUC119 DNA prepared previously. White, ampicillin-resistant colonies were selected on LB, ampicillin, Xgal, IPTG plates, and six screened for the presence of the desired DNA fragment by digestion with BamHI and PstI. All six had the desired structure, and one was saved as pWTT1028. DNA from this miniprep was used to transform the E. coli Dut−, Ung− strain BW313 (Kunkel, in Methods in Enzymology, 154:361-383, 1987) and ampicillin-resistant colonies selected. A single colony was saved for the isolation of single stranded DNA.

Single stranded DNA was isolated from BW313 cells harboring pWTT1028 as described below. The cells were grown overnight at 37° C. in 2×YT broth in the presence of ampicillin, kanamycin and the helper phage M13K07 (Vieira and Messing, 1987, supra). The cells were pelleted and the bacteriophage precipitated from the supernatant by the addition of a ¼ volume of a 2.5M NaCl, 20% polyethylene glycol (NaCl-PEG) solution and centrifugation at 8000 rpm for 10 min. The phage pellet was resuspended in 0.4 ml 2×YT transferred to an eppendorf centrifuge tube and reprecipitated with 0.1 ml of the NaCl-PEG solution. After centrifugation for 5 min. at room temperature in an eppendorf centrifuge, the supernatant was removed completely and the phage pellet suspended in 0.5 ml 0.3M Sodium Acetate, 1 mM EDTA. The DNA was extracted from the phage particles by vortexing with an equal volume of TE saturated phenol, followed by precipitation of the DNA from the aqueous phase by the addition of 1 ml of ethanol. The DNA pellet was washed with 70% ethanol, air dried and dissolved in 100 μl TE buffer. The concentration of the DNA was estimated from the UV absorbance at 260 nm.

To correctly fuse the tac promoter to the IS50R transposase, the single stranded DNA was annealed to a synthetic oligonucleotide of the following sequence:

5'TTCACACAGGAAACAGATCTTCAT-
GATAACTTCTGCT3' synthesized as described previously. This oligonucleotide was phosphorylated using T4 polynucleotide kinase as described by Maniatis. 75 pmol of phosphorylated oligonucleotide was annealed to 1 pmol of single stranded DNA of pWTT1028 by heating the mixture, (contained in a final volume of 40 μl, 5 μl of which was a buffer comprised of 1.5M KCl and 100 mM Tris pH 7.5), to 65° C. for 30 min, cooled to 37° C. for 15 min and then held at room temperature for a further 15 min. To this sample was added 4.5 μl of fill-in-buffer (comprised of 0.625M KCl, 0.275M Tris (pH 7.5), 0.15M MgCl$_2$, 20 mM dithiothreitol, 2 mM ATP, and 1 mM each of dATP, dCTP, dGTP and TTP), 7 units of Klenow polymerase, and 12 units of T4 DNA ligase. The reaction was incubated at room temperature overnight and 5 μl transformed into strain JM83. Ampicillin-resistant colonies were selected and plasmid DNA from 36 were screened for the presence of a BglII site introduced by the mutagenesis procedure. 10 of the colonies had plasmids possessing a BglII site, and these were examined for the presence of a BamHI-PstI fragment corresponding to the tac-transposase fusion. All had the appropriately sized DNA fragment and two were retained as pWTT1029 and pWTT1030.

To manipulate the 3' end of the transposase gene the terminal region of the gene was cloned from the complete Tn5 element as a PstI fragment into the vector plasmid pUC9. The appropriate PstI fragment was purified from a LMT agarose gel as described previously and ligated to 1 μg of PstI-digested pUC9 DNA in a final volume of 25 μl. The DNA was transformed into strain JM109 and white, ampicillin-resistant colonies screened for plasmid content. Of the two possible orientations of insertion of the PstI fragment in pUC9, only one was useful for subsequent manipulations. The plasmids were screened by HindIII digestion of the presence of a HindIII fragment of approx. 700 base pairs, indicative of the desired orientation of insertion. One such plasmid was saved at pWTT1005. DNA of this plasmid was transformed into the dam mutant strain of E. coli GM119 to facilitate subsequent digestions with the enzyme BclI.

The transcription-translation terminator from the bacteriophage T4 has been described by others (Prentki and Krisch, supra). Plasmid pWTT549 (patent application Ser. No. 07/357,492, the disclosure of which has previously been incorporated hereby by reference) carries the terminator fragment as a 141 base pair BamHI fragment with a HindIII site adjacent to one of its terminii. The terminator fragment was purified from 5 μg of pWTT549 plasmid DNA digested to completion with BamHI by excision of the band from a 10% polyacrylamide gel and elution into buffer as described previously. Plasmid pWTT1005 DNA was digested to completion with BamHI and BclI and the larger of the two fragments purified from a LMT agarose gel. This DNA fragment was ligated to the purified terminator fragment and transformed into JM109. Ampicillin-resistant colonies were selected and plasmid DNA from 12 were screened by digestion with BamHI. Plasmids with a single BamHI site were re-screened by digestion with HindIII for the presence of fragment of approx. 440 base pairs. Of the four colonies screened, two harbored plasmids with the desired structure, one of which was saved as pWTT1007.

To assemble the modified transposase gene, the 5' and 3' fragments from pWTT1029 and pWTT1007 respectively were ligated together at their common PstI site. DNA (10 μg) from both plasmids was digested to completion with BamHI and PstI, and the appropriate DNA fragments purified from LMT agarose gels as before. The DNAs were precipitated with ethanol and the pellets were dissolved in 50 μl TE buffer. 20 μl of each fragment preparation was ligated together overnight at room temperature in a 50 μl reaction. The ligation mix was then digested with 20 units of BamHI for 1 h at 37° C., P:C extracted, ethanol precipitated and the pellet dissolved in 50 μl TE.

These ligated transposase fragments were themselves ligated to pUC119 DNA that had been digested with BamHI and subsequently treated with alkaline phosphatase. The reaction was incubated overnight at room temperature, transformed into JM109 cells and white, ampicillin-resistant colonies selected on LBXIA plates. Plasmids from 12 such colonies were screened by digestion with BamHI, of which one had the expected DNA digestion pattern. Digestion with BglII gave two bands of the expected size, thereby verifying the nature of this plasmid. The plasmid was given the designation pWTT1032.

EXAMPLE 3. ISOLATION OF A LAC I$^q$ GENE FRAGMENT

The lacI$^q$ gene at *E. coli* is a super repressor allelle of the normal repressor of the lac promoter, and efficiently represses transcription from the tac promoter. For the construction of a transposon-delivery system, the lacI$^q$ gene was manipulated to be contained on a single restriction fragment.

The plasmid pMMB22 (Bagdasarian et al., Gene, 6:273-282, 1983) carries the lacI$^q$ gene on a single HindIII fragment. The plasmid pNMWI is a derivative of pnMMB22 that also carries a kanamycin resistance gene. pNMW1 DNA (5 μg) was digested to completion with HindIII, treated with T4 DNA polymerase to create flush ends and ligated to phosphorylated SmaI linkers. After overnight incubation at room temperature, 100U SmaI was added to the reaction and the DNA digested to completion. The 1.2 kb lacI$^q$ fragment was isolated from a 1% LMT agarose gel as described previously, and ligated with SmaI-cleaved pUC9. The ligation mix was transformed into competent cells of strain HB101 and white ampicillin-resistant cells selected on LBAp plates spread with 75 μl of 2% w/v Xgal. The presence of the lacI$^q$ gene represses the lactose operon in HB101 resulting in white colonies. Plasmid DNA from the two white colonies from this experiment were screened for the presence of a 1.2 kbSmaI fragment. One of the two was correct and was saved as pWTT624.

The lacI$^q$-containing fragment of pWTT624 contains a unique SphI site which apparently arose from the manipulations involved in its isolation from the *E. coli* chromosome. This site was removed from the subclone in pWTT624 by digestion of 5 μg of plasmid DNA to completion with SphI, then treatment with T4 DNA polymerase to create flush ends. The DNA was P:C extracted, ethanol precipitated and dissolved in 50 μl TE buffer. The plasmid DNA was ligated overnight and then subsequently digested to completion with SphI. Plasmids in which the original SphI site had been deleted will be resistant to the enzyme and transform competent cells at a high efficiency. The digested DNA was transformed into HB101 and white ampicillin-resistant colonies selected as described above. Plasmid DNA from 6 colonies was screened for the loss of the SphI site. One correct colony was saved as pWTT1051.

To assemble the components of the transposon-delivery system the three components were inserted into the same plasmid. The SmaI fragment containing the lacI$^q$ from pWTT1051 was introduced into the SmaI site of pWTT1032. 5 μg of pWTT1051 was digested with SmaI and the 1.2 kb fragment purified from LMT agarose a described previously and ligated to 1 μg SmaI-cleaved pWTT1032 DNA. The ligation mix was transformed into HB101 and plasmid DNA from white colonies on LB plates containing ampicillin and Xgal was screened for the presence of the lacI$^q$ gene fragment. One plasmid having the correct structure was saved as pWTT1052.

The XbaI fragment carrying the transposon Tn5504 element was purified by gel isolation from a complete XbaI digest of 5 μg of pWTT1059 DNA. The approx. 500 bp fragment was ligated to 1 μg of XbaI-cleaved pWTT1052 DNA for 2 h at room temperature. The ligation mix was transformed into competent cells of the strain DH5αF' (Hanahan, J. Mol. Biol., 166:557-580, 1983) and ampicillin-resistant colonies selected.

96 such colonies were screened by colony hybridization with a probe made from the oligonucleotide BT1, used to construct the transposon linker as described previously. The hybridization was performed essentially as described by Grunstein and Hogness (Proc. Na. Acad. Sci. USA 72:3961-3965, 1975) and the filter washed for 2×15 min at 65° C. The filter was exposed at −80° C. using 2 intensifying screens for 4 h, and plasmid DNA from 6 positively hybridizing colonies was analyzed for the presence of the Tn5504 fragment. One plasmid carrying an XbaI fragment of the appropriate size was saved as pWTT1060. This plasmid now carries the entire transposon delivery system on a unique KpnI-SphI restriction fragment.

To create a plasmid suitable for use as a transposon delivery vector, the KpnI-SphI fragment was introduced into the plasmid pWTT595 (U.S. patent application Ser. No. 07/357,492, the disclosure of which has previously been incorporated herein by reference). This plasmid has the EcoRI-HindIII replication fragment of plasmid pACYC184 (Chang and Cohen, J. Bacteriol., 134:1141-1156, 1974) linked to an EcoRI-HindIII fragment carrying a gentamycin resistance gene. The plasmid has unique KpnI and SphI site derived from a pUC18 polylinker region into which the Gm$^r$ fragment was previously inserted. This plasmid was chosen as it lacked any *E. coli* lac operon sequence with which the transposon Tn5504 could possible recombine and result in deletion of components of the transposon-transposase element. Aprox. 5 μg of pWTT595 and pWTT1060 DNA were digested to completion with KpnI and SphI. The transposon containing fragment from pWTT1060 was purified from a LMT agarose gel as before and ligated to the cleaved pWTT595 DNA overnight at room temperature. The mix was transformed into strain NE4 (strain MM294 recA) and white gentamycin-resistant colonies selected on LB plates containing 20 μg/ml gentamycin and spread with 75 μl of 2% (w/v) Xgal. Plasmid DNA from 6 white colonies were screened by digestion with KpnI and SphI. All had the correct structure and one was saved as plasmid pWTT1061.

To create a mobilizable transposon delivery vector, the KpnI-SphI DNA fragment carrying the various components was introduced into the vector pRLG83. pRLG83 was created by substituting the Genblock ® (Pharmacia) polylinker between the EcoRI and HindIII sites of the plasmid pBR322. pRLG83 was digested to completion with KpnI and SphI and ligated to the purified KpnI-SphI fragment from pWTT1060 described above. The ligation mix was transformed into JM109 cells and blue, ampicillin-resistant colonies selected on LB plates containing ampicillin, Xgal and IPTG. Plasmid DNA from several colonies were screened for the presence of the appropriate KpnI-SphI fragment, and one was saved as pRLG84.

EXAMPLE 5. CONSTRUCTION OF lacZΔM15 INDICATOR STRAINS. (FIG. 4)

To detect the transposition of the lacZα transposon Tn5504 to bacteriophage genomes, indicator strains were constructed which carry the lacZΔM15 allelle. The presence of the two lacZ allelles resulting in a α-complementation to a functional β-galactosidase protein has been described previously (Zabin and Fowler in the Operon eds Miller and Reznikoff, CHS Publications, Cold Spring Harbor, N.Y., pp104–107, 1978).

One approach to the construction of indicator strains is to introduce the lacZΔM15 allelle into the chromosome of a phage host using a derivative of the transposon Tn7, which inserts preferentially into a unique site in the chromosome of many Gram-negative bacteria. A Tn7-derived gene-delivery system suitable for use in Salmonella has been detailed elsewhere (Parent patent application Ser. No. 07/474,282, the disclosure of which has previously been incorporated herein by reference).

In order to create the desired strains, the lacZΔM15 allelle was first isolated from the E. coli strain JM109. To achieve, this a cosmid library in the vector pLAFR3 (Staskawicz et al., J. bacteriol. 169:5789–5794, 1987) was constructed. Total genomic DNA from JM109 was isolated as described by Maniatis et al. and subjected to partial digestion with the enzyme Sau3A. To isolate genomic fragments with a molecular weight of 20–30 kb, 1 μg samples of the JM109 DNA were digested with successively diluted aliquots of the restriction enzyme, as described by Maniatis et al. The reactions were incubated at 37° C. for 1 h and the digestion terminated by heating to 70° C. Samples of each digestion were examined by electrophoresis on a 0.6% agarose gel, and the one with the bulk of the fragments in the desired range used for construction of the library.

The two pLAFR3 arms were generated as described elsewhere (Staskawicz et al., J. bacteriol. 169:5789–5794, 1987) and used at a final concentration of 1 μg of each arm/μl. The ligation mix consisted of 1 μg of pLAFR3 arms, 1 μg Sau3A-digested JM109 genomic DNA, in a final volume of 10 μl. The reaction was incubated overnight at room temperature, and 2 μl was packaged in vitro into lambda phage particles as described elsewhere (Maniatis et al. supra). To detect the presence of the lacZΔM15 gene, the genomic library was plated onto the indicator strain WTE1000. This strain was constructed by the insertion of a Tn7-derived kanamycin resistance, lacZα-containing transposon into the chromosome of strain MC1064 (Casadaban and Cohen, J. Mol. Biol., 138:179–207, 1980). The details of the construction of the transposable elements used are described elsewhere (U.S. patent application 07/357,492, the disclosure of which has been incorporated herein by reference). Plasmid pWTT616 was transformed into strain MC1064 and kanamycin-resistant cells selected. A single colony was grown overnight in the presence of kanamycin and plated for single colonies on LB agar containing 25 μg/ml kanamycin. These colonies were screened for sensitivity to tetracycline and gentamycin (the antibiotic resistance markers of the plasmid vector), and a kanamycin-resistant, tetracycline, gentamycin sensitive colony selected and given the designation WTE1000.

The lambda library of JM109 genomic fragments was used to infect WTE1000 cells. 5 μl of the packaged library was mixed with 200 μl of exponentially growing WTE1000 cells in YM medium (Maniatis et al. supra). The cells were incubated for 30 min at 37° C., 500 μl L broth added and the incubation continued for a further 30 min. The cells were plated on LB agar plates containing 12.5 μg/ml tetracycline, Xgal and IPTG. Two blue, tetracycline-resistant colonies were observed, and plasmid DNA from these were examined by digestion with either BstEII or EcoRI. From the published nucleotide sequence of the E. coli lactose operon the desired cosmid clone should contain a BstEII fragment of approximately 6.3 kb. Both cosmid cloned gave a BstEII fragment of the expected size but showed other restriction fragment differences indicating that they had arisen from independent events. The two cosmids were saved as pWTT1018 and pWTT1019 respectively.

The BstEII fragment carrying the lacZΔM15 from plasmid pWTT1018 was modified by the addition of SmaI linkers. Plasmid DNA from pWTT1018 was digested with BstEII and subsequently treated with T4 DNA polymerase to create flush ends. The DNA was ligated overnight with 10 μl of phosphorylated SmaI linkers in a total volume of 25 ul. This mixture was then treated with 50 U of SmaI in a total volume of 50 μl and the 6.3 kb fragment purified by gel isolation as described previously. This fragment was ligated to SmaI-cleaved pUC9 DNA and the ligation mix transformed into WTE1OOO cells. Plasmid DNA from blue, ampicillin-resistant colonies were screened by digestion with SmaI. Of the six colonies screened, none had a SmaI fragment of the correct size, however 3/6 appeared to contain a lacZΔM15 fragment, one end of which had a SmaI linker attached. These 3 colonies were screened by digestion with SmaI and EcoRI to identify to which end of the BstEII fragment the SmaI linker had been attached. Two plasmids were identified which contained the SmaI linker on different ends of the original BstEII fragment, and these were saved at pWTT1022 and pWTT1023 respectively. The EcoRI-SmaI fragments carrying either end of the lacZΔM15 region were purified by gel isolation as described above. The two fragments were ligated together in a final volume of 50 μl which also included 20 U SmaI. In this way the mixture was enriched for the presence of reconstructed BstEII fragments with SmaI linkers on both ends. The ligation mix was P:C extracted and ethanol precipitated, and ligated to SmaI-cleaved pUC9 DNA. The mixture was transformed into WTE1000 cells and blue ampicillin-resistant colonies selected. Plasmid DNA from 6 such colonies was screened for the presence of a 6.3 kb SmaI fragment. Four of the six had the desired fragment and one was saved as pWTT1024.

To facilitate the insertion of the lacZΔM15 allelle into the chromosome of Salmonella, the 6.3 kb SmaI fragment was inserted into the unique PstI site of the Tn7-derived transposon delivery vector pWTT612 (U.S. patent application Ser. No. 07/357,492, the disclosure of which has been incorporated herein by reference). pWTT612 DNA (5 μg) was digested to completion with PstI and treated with T4 DNA polymerase to create flush ends. The 6.3 kb SmaI fragment from pWTT1024 was purified by gel isolation and ligated to the cleaved pWTT612 DNA. The ligation mix was transformed into WTE1000 cells and blue tetracycline-resistant colonies selected on L agar plates containing tetracycline, Xgal and IPTG. A single colony was screened to confirm the presence of a 6.3 kb BamHI-HindIII fragment which was predicted for the above manipulations. This strain was saved as pWTT1025.

Plasmid pWTT1025 was transformed together with plasmid pWTT614 (U.S. patent application Ser. No. 07/357,492, the disclosure of which has been incorporated herein by reference) into the recombination-proficient strain of *E. coli*, JM83 (Vieira and Messing, Gene 19:259-269, 1982). Transformants resistant to tetracycline and gentamycin were selected and streaked onto LB plates containing ampicillin. This selects for in vivo recombinants between the two plasmids, each of which carry a partial β-lactamase gene. The recombinant ampicillin-resistant plasmid was designated pWTT1034.

To create a chromosomal insertion of the lacZΔM15 region, plasmid pWTT1034 was introduced by conjugation into a derivative of *S. typhimurium* strain LT2, selected for spontaneous resistance to 25 μg/ml spectinomycin. Transconjugants were selected on L agar plates containing tetracycline, gentamycin and spectinomycin. Single colonies from the selective plates were inoculated into 5 ml of L broth and grown overnight at 37° C. This culture was then plated for single colonies on L agar plates at 37° C. and these colonies subsequently tested for their antibiotic resistance phenotype. 48 tetracycline sensitive cells were screened by colony hybridization as described previously to a probe made by nick translation (Rigby et al. J. Mol. Biol. 113:239-251, 1977) from plasmid pWTT1024. Two strongly hybridizing colonies were observed and were given the designation WTS1000 and WTS1001. These strains were tested for their ability to act as indicator strains by the introduction into each by conjugation of the plasmid pWTT1011, which carries a lacZα gene fragment. Transconjugants of both strains utilized lactose, growing well on M9 minimal plates (Miller, supra) containing lactose as a sole source of carbon.

EXAMPLE 6. TRANSPOSITION OF Tn5504 TO PHAGE P22

Plasmid pWTT1061 was first transformed into the restrictionless mutant strain of *S. typhimurium* LB5000 (Sanderson and Stocker, in *Escherichia coli* and *Salmonella typhimurium*: Cellular and Molecular Biology, eds Niedhardt et al. American Society for Microbiology, Washington, D.C. Vol2, pp1220-1224, 1987), and gentamycin-resistant colonies selected at 37° C. A single colony was saved as WTS1014. Plasmid DNA was extracted from WTS1014 by the method of Birmboim and Doly (supra) and used to transform strain RGS6, a P22 lysogen of *S. typhimurium* LT2. A single gentamycin-resistant colony was selected and grown overnight at 37° C. in L broth containing gentamycin and IPTG (to induce the transposase). This culture was used to inoculate a second L broth gentamycin IPTG culture which was grown with shaking at 37° C. to an $A_{550}$ of 0.5. Mitomycin C was added to the culture to a final concentration of 5 μg/ml and the culture then incubated in the dark for a further 2-3 hours until lysis occurred.

To pellet the cellular debris, the lysate was centrifuged at approx. 8000XG for 10 min, and the supernatant passed through a 0.22 μm filter to remove any remaining bacteria. To remove any residual mitomycin C from the bacteriophage lysate, 0.125 ml NaCl-PEG was added to 0.5 ml of the filtered supernatant, and the phage pelleted by centrifugation for 10 minutes in an eppendorf centrifuge. The phage pellet was resuspended in 100 μl of lambda dilution buffer (Maniatis et al. supra).

For detection of transposon insertions into P22, 100 μl of a series of 10 fold dilutions of the phage preparation was mixed with 100 μl of logarithmically growing cells of strain WTS1000, and incubated at room temperature for 30-60 min. To each reaction 100 μl of a preparation of heat killed WTS1000 cells (prepared by concentrating a stationary phase culture of WTS1000 ten fold and heating in a boiling water bath for 20 min.) was added and the mixture plated on M9 minimal plates containing lactose as the sole carbon source. These plates were incubated at 37° C. for 48 h and examined for the appearance of Lac+ colonies. In addition, 100 μl dilutions of the phage preparation were mixed with 100 μl of log phase WTS1000 cells, added to 3 ml of 0.6% L agar and spread on the surface of L agar plates to determine the titre of viable phage in the preparation.

The induced phage preparation from the experiment described above had a titre of approximately $5 \times 10^7$ plaque forming units (pfu)/ml. A single colony was observed on the M9 lactose plate from the undiluted phage preparation (approximately $5 \times 10^6$ pfu) This colony was tested for gentamycin resistance, and was found to be sensitive to the antibiotic, thereby eliminating the possibility that it had arisen from a generalized transduction of pWTT1061 by phage P22.

This strain was then subjected to a second round of mitomycin C induction and the culture centrifuged and filtered as before. The supernatant was serially diluted in buffer and plated for single plaques on WTS1000 lawns as described above except that 100 μl Xgal was included in each overlay. After overnight incubation at 37° C. a mixture of blue and white phage plaques were observed at a ratio of 1:3. The lysogenic cells from the center of a blue plaque were streaked for single colonies on L agar plates containing Xgal at 37° C., and gave a mixture of white and blue colonies. Isolated blue colonies were again subjected to a round of plate purification and now yielded only blue colonies on the L agar Xgal medium. When phage were prepared by mitomycin C induction of the pure blue colonies, all yielded only blue plaques on WTS1000 lawns in the presence of Xgal. The lysogenic strain carrying the presumed Tn5504 insertion into P22 was designated WTS1016, and the phage itself P22::Tn5504-1.

The transposon-tagging experiment described above was repeated, and yielded a further two P22::Tn5504 insertions, P22::Tn5504-2 and P22::Tn5504-3. DNA was extracted from induced lysates of the three P22::Tn5504 insertions by digestion of the crude lysate with 0.1 vol of 10 mg/ml proteinase K for 2 h at 37° C. followed by 2 successive extractions with an equal volume of phenol:chloroform (1:1). The DNA was precipitated from the aqueous phase with ethanol and the pellet dissolved in TE buffer. Digestion of the DNA with either EcoRI or HindIII indicated that the transposon had inserted into different sites in the P22 genome, all of which were clustered in the same region of the phage genome.

EXAMPLE 7. TRANSPOSITION OF Tn5504 TO PHAGE 98

Phage 98 lysogenizes strains of Salmonella in the Kaufmann-White serogroup C2 (Le Minor, in Bergey's Manual of Determinative Bacteriology, Vol1, eds Kreig and Holt, Williams and Wilkins, Baltimore, Md., pp427-458, 1984). It is uncharacterized at the molecular level. A lysogen of phage 98 in the Salmonella strain BS68, a derivative of the strain *S. bovismorbificans*

SL5747 (received from B. Stocker) cured of its indigenous resistance to tetracycline and streptomycin by treatment with acridine orange, was isolated from the center of a turbid plaque. Into this strain was introduced by conjugation the plasmid pRLG84, carrying the Tn5505 delivery system. Cells were grown overnight in L broth and used to inoculate a second 5 ml L broth culture containing 25 μl 2% (w/v) IPTG. The cells were grown to an $A_{550}$ of approx. 0.5 and induced for phage lysis by the addition of mitomycin C as described above. The phage lysate was purified as before and used to transduce strain BS79, a derivative of BS68 carrying a transposon Tn7-mediated insertion of the lacZΔM15 in its chromosome, constructed as described in Example 5. The transduction was performed as described in Example 6, with the substitution of BS79 for the *S. typhimurium* LT2 derivative strains. Single Lac+ colonies were observed on the transduction plates and these yielded strains which were lysogenic for phage 98 carrying insertions of transposon Tn5504.

EXAMPLE 8. CONSTRUCTION OF A MARKER EXCHANGE VECTOR FOR THE INSERTION OF AN inaW GENE INTO P22::Tn5504

To insert the inaW gene into the genome of phage P22 at the site identified by the insertion of Tn5504, a plasmid vector was constructed from the plasmid pCM301 (Tucker et al. Cell, 38:191-201, 1984). This plasmid, derived from plasmid pSC101 (Cohen and Chang, J. Bacteriol., 132:734-737, 1977) is a temperature-sensitive replication mutant resistant to ampicillin. Into the unique EcoRI site of pCM301 was inserted the XbaI fragment carrying Tn5504.

pCM301 DNA (5 μg) was digested to completion with EcoRI and treated with T4 DNA polymerase to create flush ends as described previously. The approx. 500 bp fragment carrying Tn5504 was isolated from a complete XbaI digest of plasmid pWTT1059 which had been also subsequently treated with T4 DNA polymerase by extraction from a LMT agarose gel as described previously. The two DNAs were ligated together, the mixture transformed into JM109 cells, and blue, ampicillin-resistant cells selected on L agar plates containing ampicillin, Xgal and IPTG. Plasmid DNA from 6 such colonies was screened for the presence of an XbaI fragment of the appropriate size, and for the presence of EcoRI fragments corresponding to reconstruction of the EcoRI site in the vector and the presence of a single EcoRI site in the lacZα gene fragment. Of the 6 colonies screened, 4 had carried plasmids of the desired structure and one such plasmid was saved and given the designation pWTT1064.

The inaW gene used in the construction of the marker exchange plasmid was modified to be expressed from the synthetic tac promoter (as described in detail in the Experimental section of parent application Ser. No. 07/474,282, the disclosure of which has previously been incorporated herein by reference). The gene was isolated as a BamHI-HindIII restriction enzyme fragment from the plasmid pRLG67, by gel isolation as described above. A HindIII-BamHI restriction enzyme fragment of plasmid pWTT551 (U.S. patent application Ser. No. 07/357,492, the disclosure of which has previously been incorporated herein by reference) carrying the T4 transcription-translation terminator region described earlier was isolated from a 10% polyacrylamide gel as detailed previously. The two DNA fragments were ligated together overnight at room temperature and subsequently digested with the enzyme BamHI. The mixture was P:C extracted and ethanol precipitated and the DNA ligated to a BamHI-cleaved preparation of the plasmid pVSP61. The mixture was transformed into cells of strain JM109, and a blue, kanamycin-resistant, Ina+ colonies screened for plasmid content. The plasmid DNA from this colony, when digested with BamHI, gave a fragment pattern consistent with the insertion of tac-inaW-T4 terminator fragment into pVSP61. This plasmid was designated PWTT1067.

The DNA fragment carrying the inaW gene from pWTT1067 was purified by gel isolation from a complete BamHI digest of 5 μg of plasmid DNA which had been subsequently treated with T4 DNA polymerase to create flush ends, as described before. This fragment was ligated to SmaI-cleaved DNA of plasmid pWTT1064 and transformed into JM109 cells. Plasmid DNA from two white, ampicillin-resistant Ina+ cells were analyzed by restriction enzyme digestion with EcoRI and SalI for DNA fragments of the predicted size. One of the two had the predicted structure and was designated pWTT1069.

EXAMPLE 9. CONSTRUCTION OF HIGH-FREQUENCY inaW TRANSDUCING PARTICLES

Plasmid pWTT1069 was introduced into *S. typhimurium* LB5000 by transformation, and plasmid DNA prepared from this strain. This DNA preparation was used to transform competent cells of WTS1016 and blue, ampicillin-resistant cells selected on L agar plates containing ampicillin, Xgal and IPTG at 28° C. All such colonies were tested for Ina phenotype and were Ina+. Six of these colonies were themselves restreaked for single colonies on L agar containing ampicillin and incubated at 42° C. Plasmid pWTT1069 is unable to replicate at 42° C., therefore ampicillin-resistant cells result from a rescue of the plasmid replicon by recombination with the homologous sequences present in the prophage genome to give a co-integrate structure. A single ampicillin-resistant colony from each of the original 6 transformants was selected and purified by again streaking for single colonies on ampicillin plates at 42° C.

Each of these 6 putative cointegrates was grown in LB at 37° C. and induced for phage lysis by the addition of mitomycin C as described above. The phage lysates were centrifuged and filter sterilized as before and used to transduce the inaW gene to cells of *S. typhimurium* LT2. A 100 μl volume of each lysate or 10 fold dilutions of same was mixed with 100 μl of exponentially growing WTS1000 cells. The mixtures were incubated for 1 h at 37° C. and then 1 h at room temperature, before being aliquoted in 10 μl drops on the surface of a paraffin coated sheet of aluminum foil placed on the surface of a circulating cold bath at −10° C. The number of drops frozen at each dilution of the initial phage preparation were counted, and the number of transducing particles in each initial phage preparation estimated using Most Probable Number statistics. A sample of each phage preparation was also titred for pfu on lawns of WTS1000 cells. The results are given in Table 2.

TABLE 2

| Isolate No. | $TP^a$/ml | pfu/ml |
|---|---|---|
| 1 | $9.1 \times 10^2$ | $3.8 \times 10^8$ |
| 2 | $3.5 \times 10^4$ | $8.0 \times 10^3$ |
| 3 | $1.2 \times 10^5$ | $3.0 \times 10^5$ |

TABLE 2-continued

| | | |
|---|---|---|
| 4 | $2.2 \times 10^5$ | $1.0 \times 10^5$ |
| 5 | $7.0 \times 10^4$ | $2.0 \times 10^4$ |
| 6 | $1.2 \times 10^5$ | $5.0 \times 10^4$ |

$^a$ina transducing particles

The number of transducing particles is given by the formula:

$$[\text{ina}] = 1/V_d \times \ln(N_t/N_u)$$

where: $V_d$ = volume of the drop tested;
$N_t$ = total number of drops tested; and
$N_u$ = number of drops unfrozen.

The isolates which give a high TP/pfu ratio were presumed to have cointegrate structures formed by recombination between the transposon present in the prophage genome and pWTT1069.

To screen for resolution of the cointegrate and the resulting marker exchange of the inaW gene into the prophage, the six isolates were grown overnight in L broth at 42° C. The cultures were then plated for single colonies on L agar plates spread with Xgal. Resolved cointegrates in which the inaW gene has been introduced into the prophage should be white, ampicillin sensitive and Ina+. Of the six strains tested, only one gave white colonies. Six of these white colonies were tested and all possessed the expected phenotype.

These six strains were induced for phage lysis as before and the supernatants tested for the presence of transducing particles and plaque forming particles as described above. The results are given in Table 3.

TABLE 3

| Isolate No. | TP/ml | pfu/ml |
|---|---|---|
| 1 | $6.9 \times 10^4$ | $5.0 \times 10^2$ |
| 2 | $9.1 \times 10^4$ | $5.0 \times 10^2$ |
| 3 | $1.1 \times 10^5$ | $1.0 \times 10^3$ |
| 4 | $1.2 \times 10^5$ | $1.5 \times 10^3$ |
| 5 | $9.1 \times 10^5$ | $1.0 \times 10^3$ |
| 6 | $5.1 \times 10^5$ | $1.5 \times 10^3$ |

As predicted, all the presumed resolved cointegrates tested showed a TP/pfu ratio of >1. This occurs because the insertion of the inaW gene into the prophage genome causes the total size of the phage DNA to exceed the packaging limits of the viral head, such that most of the particles produced are defective because they lack some of the genes essential to complete the viral life cycle.

Although the foregoing invention has been described in some detail by way of illustration and example for purposes of clarity of understanding, it will be obvious that certain changes and modifications may be practiced within the scope of the appended claims.

What is claimed is:

1. A method for producing a transducing particle, said method comprising:
    introducing DNA sequences into a bacterial host, wherein the host carries a prophage in its genome and the DNA sequences include (a) a pair of transposable element terminal sequences having a selectable marker sequence therebetween and (b) a transposase gene located outside of the transposase element terminal sequences, whereby the marker sequence can become incorporated within the prophage;
    inducing the prophage to a lytic cycle, whereby transducing particles are released;
    selecting viable transducing particles which carry the selectable marker sequence; and
    introducing a screenable marker gene to a selected transducing particle.

2. A method as in claim 1, wherein the transposable element terminal sequences, marker sequence, and transposase gene are present on a single bacterial vector which is introduced to the host, with the transposase gene located outside of the terminal sequences.

3. A method as in claim 1, wherein the transposable element terminal sequences and marker sequence are present on one bacterial vector which is introduced to the host and the transposase gene is present on another bacterial vector which is introduced to the host.

4. A method for producing a transducing particle, said method comprising:
    introducing a bacterial vector to a bacterial host, wherein:
    (a) the bacterial vector includes a pair of transposable element terminal sequences, a selectable marker sequence disposed between the terminal sequences, and a transposase gene outside of the terminal sequences; and
    (b) the bacterial host carries a prophage in the bacterial genome, whereby the transposable elements can transpose the marker sequence to the prophage;
    inducing the prophage to a lytic cycle, whereby transducing particles which carry the marker sequence are produced;
    selecting transducing particles which carry the selectable marker sequence; and
    introducing a screenable marker sequence to the selected transducing particles.

5. A method as in claim 4, wherein the screenable marker sequence is capable of expressing a visually observable phenotype in viable bacterial host cells.

6. A method as in claim 4, wherein the selectable marker sequence is capable of conferring viability to the bacterial host grown under controlled conditions.

7. A method as in claim 6, wherein the selectable marker sequence is the lacZ α fragment.

8. A method as in claim 4, wherein the screenable marker sequence is introduced by substitution for the selectable marker sequence in the transducing particle.

9. A method as in claim 8, wherein the selectable marker sequence is substituted by homologous recombination.

10. A method as in claim 4, wherein the prophage is P22.

11. A method as in claim 4, wherein the transposable element terminal sequences are derived from Tn5.

12. A method as in claim 4, wherein the bacterial host is E. coli.

13. A method as in claim 4, further comprising inducing transposition prior to inducing the prophage to a lytic cycle.

14. A method as in claim 13, wherein inducing transposition comprises elimination of repression.

15. A method for producing a transducing particle, said method comprising:
    inducing a prophage in a bacterial host to a lytic cycle to release the transducing particles, said prophage including a screenable marker sequence flanked by a pair of transposable element terminal sequences and lacking a transposase gene.

16. A method as in claim 15, wherein the lytic cycle is induced by a change in temperature, by a chemical inducer, or by exposure to ultraviolet radiation.

17. A method as in claim 15, wherein the screenable marker sequence is capable of expressing a visually observable phenotype in a preselected host.

18. A method as in claim 17, wherein the visually observable phenotype is selected from the group consisting of bioluminescence, fluorescence, enzyme catalyzed color production, and ice nucleation activity.

19. A method as in claim 15, wherein the transducing particles are capable of specifically infecting gram negative bacteria selected from the group consisting of *Escherichia coli*, *Vibrio cholera*, Salmonella, and Helicobacter.

20. A method as in claim 15, wherein the transducing particles are capable of specifically infecting gram positive bacteria selected from the group consisting of *Staphylococcus aureus*, *Streptocossus pyogenes* and *Listeria monocytogenes*.

21. A transducing particle comprising a proteinaceous coat and a DNA core including a pair of transposable element terminal sequences and a screenable marker sequence between said terminal sequences, wherein the DNA core does not include a functional transposage gene or a selectable marker sequence.

22. A transducing particle as in claim 21, wherein the screenable marker sequence is present between restriction sites which in turn are between the terminal sequences.

23. A transducing particle as in claim 21, wherein the screenable marker sequence is capable of expressing a visually observable phenotype in viable cells of a bacterial host with the host range of the transducing particle.

24. A transducing particle as in claim 23, wherein the visually observable phenotype is selected from the group consisting of bioluminescence, fluorescence, enzyme-catalyzed color production, and ice nucleation activity.

25. A transducing particle as in claim 21, wherein the transducing particles are capable of specifically infecting gram negative bacteria selected from the group consisting of *Escherichia coli, Vibrio cholera*, Salmonella, and Helicobacter.

26. A transducing particle as in claim 21, wherein the transducing particles are capable of specifically infecting gram positive bacteria selected from the group consisting of *Staphylococcus aureus* and *Streptococcus pyogenes* and *Listeria monocytogenes*.

27. A bacterial host having a prophage in the bacterial genome, wherein the prophage carries a transposable element which includes a screenable marker sequence but which does not include a selectable marker sequence and is defective and unable to transpose.

28. A bacterial host as in claim 27, wherein the screenable marker sequence is disposed between restriction sites.

29. A bacterial host as in claim 27, wherein the screenable marker sequence has fewer than 1000 bp.

30. A bacterial host as in claim 27, wherein the screenable marker sequence has more than 1000 bp.

31. A bacterial host as in claim 30, wherein the screenable marker sequence is a gene capable of conferring a visually detectable phenotype selected from the group consisting of bioluminescence, fluorescence, enzyme-catalyzed color production, and ice nucleation activity.

32. A method for producing transducing particles capable of conferring an ice nucleation phenotype on infected bacterial cells, said method comprising:
    combining a gene encoding the ice nucleation phenotype with the essential terminal DNA sequences of a transposon to produce an insertable element; and
    introducing the insertable element into a bacteriophage having a genome capable of recombination with the insertable element.

33. A method as in claim 32, wherein the insertable element is present in a bacterial plasmid and introduced to the bacteriophage by recombination in a bacterial cell.

34. A method for detecting antibiotic residues in a sample, said method comprising:
    exposing a portion of the sample to a culture comprising bacteria sensitive to the antibiotic;
    introducing to the culture a transducing particle produced by the method of claim 1, wherein the transducing particle is capable of infecting the bacteria in the culture;
    determining whether the marker sequence is being expressed, where such expression is indicative that insufficient antibiotic residue is present to kill the bacteria.

35. A method as in claim 34, wherein the marker gene is an ice nucleation gene and expression of the gene is determined by a freezing assay.

* * * * *